United States Patent
Heruth et al.

(10) Patent No.: US 10,251,595 B2
(45) Date of Patent: *Apr. 9, 2019

(54) COLLECTING GAIT INFORMATION FOR EVALUATION AND CONTROL OF THERAPY

(71) Applicant: Medtronic, Inc., Minneapolis, MN (US)

(72) Inventors: Kenneth T. Heruth, Edina, MN (US); Keith A. Miesel, St. Paul, MN (US); Gregory F. Molnar, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 43 days.

This patent is subject to a terminal disclaimer.

(21) Appl. No.: 15/439,152

(22) Filed: Feb. 22, 2017

(65) Prior Publication Data

US 2017/0156663 A1 Jun. 8, 2017

Related U.S. Application Data

(63) Continuation of application No. 14/278,821, filed on May 15, 2014, now Pat. No. 9,592,379, which is a
(Continued)

(51) Int. Cl.
*A61N 1/37* (2006.01)
*A61B 5/00* (2006.01)
(Continued)

(52) U.S. Cl.
CPC .......... *A61B 5/4836* (2013.01); *A61B 5/0022* (2013.01); *A61B 5/0031* (2013.01);
(Continued)

(58) Field of Classification Search
CPC .......... A61B 5/1038; A61B 2562/0219; A61N 1/36067; A61N 1/36003
See application file for complete search history.

(56) References Cited

U.S. PATENT DOCUMENTS

| 4,297,685 A | 10/1981 | Brainard, II |
| 4,550,736 A | 11/1985 | Broughton et al. |
(Continued)

FOREIGN PATENT DOCUMENTS

| DE | 19831109 A1 | 1/2000 |
| DE | 10024103 A1 | 11/2001 |
(Continued)

OTHER PUBLICATIONS

"Analysis of heart rate dynamics by methods derived from nonlinear mathematics: Clinical applicability and prognostic significance," http://herkules.oulu.fi.isbn9514250133/html, Oct. 2004, 4 pp.

(Continued)

*Primary Examiner* — Tammie K Marlen
(74) *Attorney, Agent, or Firm* — Shumaker & Sieffert, P.A.

(57) ABSTRACT

A medical device delivers a therapy to a patient. The medical device or another device may periodically determine an activity level or gait parameter of the patient, and associate each determined level or parameter with a current therapy parameter set. A value of at least one activity metric is determined for each of a plurality of therapy parameter sets based on the activity levels or parameters associated with that therapy parameter set. Whether the patient is currently experiencing or anticipated to experience gait freeze caused by their neurological disorder, such as Parkinson's disease, may also be determined. Gait freeze events may be associated with current therapy parameters and used to determine activity metric values. In some examples, the activity metric associated with certain therapy parameters may be presented to a user.

20 Claims, 16 Drawing Sheets

Related U.S. Application Data continuation of application No. 11/691,423, filed on Mar. 26, 2007, now Pat. No. 8,744,587.

(60) Provisional application No. 60/785,658, filed on Mar. 24, 2006.

(51) Int. Cl.

| | |
|---|---|
| *A61B 5/0488* | (2006.01) |
| *A61B 5/103* | (2006.01) |
| *A61N 1/36* | (2006.01) |
| *A61B 5/03* | (2006.01) |
| *A61B 5/11* | (2006.01) |
| *A61M 5/172* | (2006.01) |
| *G06F 19/00* | (2018.01) |

(52) U.S. Cl.
CPC ............ *A61B 5/031* (2013.01); *A61B 5/0488* (2013.01); *A61B 5/1038* (2013.01); *A61B 5/112* (2013.01); *A61B 5/1123* (2013.01); *A61B 5/4082* (2013.01); *A61B 5/4094* (2013.01); *A61B 5/7246* (2013.01); *A61B 5/7275* (2013.01); *A61B 5/7282* (2013.01); *A61B 5/742* (2013.01); *A61B 5/7405* (2013.01); *A61B 5/7455* (2013.01); *A61M 5/1723* (2013.01); *A61N 1/36003* (2013.01); *A61N 1/3615* (2013.01); *A61N 1/36067* (2013.01); *G06F 19/00* (2013.01); *A61B 2562/0219* (2013.01); *A61N 1/36082* (2013.01)

(56) References Cited

U.S. PATENT DOCUMENTS

| | | | |
|---|---|---|---|
| 4,771,780 A | 9/1988 | Sholder |
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,509,927 A | 4/1996 | Epstein et al. |
| 5,514,162 A | 5/1996 | Bornzin et al. |
| 5,591,216 A | 1/1997 | Testerman et al. |
| 5,593,431 A | 1/1997 | Sheldon |
| 5,622,428 A | 4/1997 | Bonnet |
| 5,645,053 A | 7/1997 | Remmers et al. |
| 5,683,432 A | 11/1997 | Goedeke et al. |
| 5,713,923 A | 2/1998 | Ward et al. |
| 5,732,696 A | 3/1998 | Rapoport et al. |
| 5,782,884 A | 7/1998 | Stotts et al. |
| 5,814,093 A | 9/1998 | Stein |
| 5,833,709 A | 11/1998 | Rise et al. |
| 5,851,193 A | 12/1998 | Arikka et al. |
| 5,895,371 A | 4/1999 | Levitas et al. |
| 5,904,708 A | 5/1999 | Goedeke |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,006,124 A | 12/1999 | Fischell et al. |
| 6,044,297 A | 3/2000 | Sheldon et al. |
| 6,045,513 A | 4/2000 | Stone et al. |
| 6,059,576 A | 5/2000 | Brann |
| 6,091,973 A | 7/2000 | Colla et al. |
| 6,094,598 A | 7/2000 | Elsberry et al. |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,161,095 A | 12/2000 | Brown |
| 6,165,143 A | 12/2000 | Van Lummel |
| 6,227,203 B1 | 5/2001 | Rise et al. |
| 6,259,948 B1 | 7/2001 | Florio et al. |
| 6,273,856 B1 | 8/2001 | Sun et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,433,690 B2 | 8/2002 | Petelenz et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,234 B1 | 10/2002 | Van der Loos et al. |
| 6,466,821 B1 | 10/2002 | Pianca et al. |
| 6,468,234 B1 | 10/2002 | Van der Loos et al. |
| 6,473,639 B1 | 10/2002 | Fischell et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,597,954 B1 | 7/2003 | Pless et al. |
| 6,605,038 B1 | 8/2003 | Teller et al. |
| 6,611,783 B2 | 8/2003 | Kelly, Jr. et al. |
| 6,626,902 B1 | 9/2003 | Kucharczyk et al. |
| 6,659,968 B1 | 12/2003 | McClure |
| 6,665,558 B2 | 12/2003 | Kalgren et al. |
| 6,687,538 B1 | 2/2004 | Hrdlicka et al. |
| 6,731,984 B2 | 5/2004 | Cho et al. |
| 6,735,474 B1 | 5/2004 | Loeb et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,937,891 B2 | 8/2005 | Leinders et al. |
| 6,964,641 B2 | 11/2005 | Cho et al. |
| 6,993,380 B1 | 1/2006 | Modarres |
| 7,130,689 B1 | 10/2006 | Turcott |
| 7,141,034 B2 | 11/2006 | Eppstein et al. |
| 7,151,961 B1 | 12/2006 | Whitehurst et al. |
| 7,155,279 B2 | 12/2006 | Whitehurst et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,209,787 B2 | 4/2007 | DiLorenzo |
| 7,309,314 B2 | 12/2007 | Grant et al. |
| 7,313,440 B2 | 12/2007 | Miesel |
| 7,330,760 B2 | 2/2008 | Heruth et al. |
| 7,366,572 B2 | 4/2008 | Heruth et al. |
| 7,395,113 B2 | 7/2008 | Heruth et al. |
| 7,415,308 B2 | 8/2008 | Gerber et al. |
| 7,447,545 B2 | 11/2008 | Heruth et al. |
| 7,468,040 B2 | 12/2008 | Hartley et al. |
| 7,491,181 B2 | 2/2009 | Heruth et al. |
| 7,542,803 B2 | 6/2009 | Heruth et al. |
| 7,580,752 B2 | 8/2009 | Gerber et al. |
| 7,590,453 B2 | 9/2009 | Heruth et al. |
| 7,590,455 B2 | 9/2009 | Heruth et al. |
| 7,717,848 B2 | 5/2010 | Heruth et al. |
| 7,787,946 B2 | 8/2010 | Stahmann et al. |
| 7,792,583 B2 | 9/2010 | Miesel et al. |
| 7,805,196 B2 | 9/2010 | Miesel et al. |
| 7,853,322 B2 | 12/2010 | Bourget et al. |
| 7,860,561 B1 | 12/2010 | Modarres |
| 7,881,798 B2 | 2/2011 | Heruth et al. |
| 7,908,013 B2 | 3/2011 | Miesel et al. |
| 8,032,224 B2 | 10/2011 | Miesel et al. |
| 8,073,534 B2 | 12/2011 | Low |

(56) References Cited

U.S. PATENT DOCUMENTS

| | | |
|---|---|---|
| 8,190,253 B2 | 5/2012 | Heruth et al. |
| 8,244,340 B2 | 8/2012 | Wu et al. |
| 8,285,372 B2 | 10/2012 | Sing |
| 8,308,661 B2 | 11/2012 | Miesel et al. |
| 8,335,568 B2 | 12/2012 | Heruth et al. |
| 8,337,431 B2 | 12/2012 | Heruth et al. |
| 8,725,244 B2 | 5/2014 | Miesel et al. |
| 8,744,587 B2 | 6/2014 | Miesel et al. |
| 8,758,242 B2 | 6/2014 | Miesel et al. |
| 9,205,264 B2 | 12/2015 | Heruth et al. |
| 9,592,379 B2 | 3/2017 | Heruth et al. |
| 2001/0031930 A1 | 10/2001 | Roizen et al. |
| 2001/0037067 A1 | 11/2001 | Tchou et al. |
| 2001/0041831 A1 | 11/2001 | Starkweather et al. |
| 2001/0049471 A1 | 12/2001 | Suzuki et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0135917 A1 | 7/2003 | Ruane |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0204219 A1 | 10/2003 | Gielen |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0077995 A1 | 4/2004 | Ferek-Petric et al. |
| 2004/0088025 A1 | 5/2004 | Gesotti |
| 2004/0102814 A1 | 5/2004 | Sorenson et al. |
| 2004/0111040 A1 | 6/2004 | Ni et al. |
| 2004/0111041 A1 | 6/2004 | Ni et al. |
| 2004/0138719 A1 | 7/2004 | Cho et al. |
| 2004/0199217 A1 | 10/2004 | Lee et al. |
| 2004/0215269 A1 | 10/2004 | Burnes et al. |
| 2004/0220621 A1 | 11/2004 | Zhou et al. |
| 2005/0021103 A1 | 1/2005 | DiLorenzo |
| 2005/0021104 A1 | 1/2005 | DiLorenzo |
| 2005/0039745 A1 | 2/2005 | Stahmann et al. |
| 2005/0042589 A1 | 2/2005 | Hatlestad et al. |
| 2005/0060001 A1 | 3/2005 | Singhal et al. |
| 2005/0061320 A1 | 3/2005 | Lee et al. |
| 2005/0065560 A1 | 3/2005 | Lee et al. |
| 2005/0076908 A1 | 4/2005 | Lee et al. |
| 2005/0080463 A1 | 4/2005 | Stahmann et al. |
| 2005/0081847 A1 | 4/2005 | Lee et al. |
| 2005/0085738 A1 | 4/2005 | Stahmann et al. |
| 2005/0113710 A1 | 5/2005 | Stahmann et al. |
| 2005/0115561 A1 | 6/2005 | Stahmann et al. |
| 2005/0119703 A1 | 6/2005 | DiLorenzo |
| 2005/0143617 A1 | 6/2005 | Auphan |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0235472 A1 | 10/2006 | Goetz et al. |
| 2006/0293720 A1 | 12/2006 | DiLorenzo |
| 2007/0038265 A1 | 2/2007 | Tcheng et al. |
| 2007/0046408 A1 | 3/2007 | Shim |
| 2007/0073355 A1 | 3/2007 | DiLorenzo |
| 2007/0142862 A1 | 6/2007 | DiLorenzo |
| 2007/0255118 A1 | 11/2007 | Miesel et al. |
| 2007/0276439 A1 | 11/2007 | Miesel et al. |
| 2008/0154111 A1 | 6/2008 | Wu et al. |
| 2009/0030263 A1 | 1/2009 | Heruth et al. |
| 2009/0036951 A1 | 2/2009 | Heruth et al. |
| 2009/0082691 A1 | 3/2009 | Denison et al. |
| 2009/0099627 A1 | 4/2009 | Molnar et al. |
| 2013/0150921 A1 | 2/2013 | Singhal et al. |
| 2013/0331906 A1 | 12/2013 | Krueger et al. |
| 2014/0222101 A1 | 8/2014 | Miesel et al. |
| 2016/0158552 A1 | 6/2016 | Heruth et al. |
| 2016/0263382 A1 | 9/2016 | Heruth et al. |
| 2017/0165481 A1 | 6/2017 | Menon |

FOREIGN PATENT DOCUMENTS

| | | |
|---|---|---|
| EP | 0564803 A1 | 10/1993 |
| EP | 0849715 B1 | 6/1998 |
| EP | 1195139 A1 | 4/2002 |
| EP | 1291036 A2 | 3/2003 |
| EP | 1308182 A2 | 5/2003 |
| EP | 1437159 A1 | 7/2004 |
| EP | 1322227 B1 | 12/2005 |
| GB | 2330912 A | 5/1999 |
| WO | 1998/000197 A1 | 1/1998 |
| WO | 1999/013765 A1 | 3/1999 |
| WO | 2001/037930 A1 | 5/2001 |
| WO | 2002/028282 A1 | 4/2002 |
| WO | 2002/041771 A1 | 5/2002 |
| WO | 2002/087433 A1 | 11/2002 |
| WO | 2002/0096512 A1 | 12/2002 |
| WO | 2002/0100267 A1 | 12/2002 |
| WO | 2003/024325 A2 | 3/2003 |
| WO | 2003/051356 A1 | 6/2003 |
| WO | 2003/065891 A2 | 8/2003 |
| WO | 2005/028029 A2 | 3/2005 |
| WO | WO 2005/020866 | 3/2005 |
| WO | 2005/035050 A1 | 4/2005 |

OTHER PUBLICATIONS

"Bilateral Comparisons of the BiteStrip Bruxism Device and Masseter EMG Bruxism Events," downloaded from Internet Archive of www.quietsleep.com dated Jan. 29, 2005, http://web.archive.org/web/20041124075114/www.quietsleep.com/pdf/Bilateral+Comparisons.pdf, 1 pp.

"Bitestrip Flier," downloaded from Internet Archive of www.quietsleep.com dated Jan. 29, 2005, http://web.archive.org/web/20041124080003/www.quietsleep.com/pdf/bitestrip+Flier.pdf., 1 pp.

"The BiteStrip: A Novel Screener for Sleep Bruxism," downloaded from Internet Archive of www.quietsleep.com dated Jan. 29, 2005, https://web.archive.org/web/20041124072922/www.quietsleep.com/pdf/BiteStrip-+Novel+Screener.pdf.

"Design Competition: Runners-Up for the Best Three Designs," EPN, vol. 26, No. 1, Jan. 2002, 1 pp.

"IBM & Citizen Watch develop Linux-based 'WatchPad'," http://www.linuxdevices.com/news/NS6580187845.html, Retrieved on Feb. 20, 2006, 5 pp.

"MiniMitter® Physiological and Behavioral Monitoring for Humans and Animals," http://www.minimitter.com/Products/Actiwatch, Retrieved on Feb. 20, 2006, 3 pp.

"The BiteStrip: A Novel Screener for Sleep Bruxism," downloaded from Internet Archive of www.quietsleep.com dated Jan. 29, 2005,

(56) References Cited

OTHER PUBLICATIONS http://http.web.archive.org/web/20041124072922/www.quietsleep.com/pdf/BiteStrip-+Novel+Screener.pdf., 1 pp.
"Watch,"Wikipedia, the free encyclopedia, http://en.wikipedia.org/wiki/Watch, Feb. 20, 2006, 6 pp.
Aminian et al., "Physical Activity Monitoring Based on Accelerometry: Validation and Comparison with Video Observation," Medical & Biological Engineering & Computing, vol. 37, No. 2, Mar. 1999, pp. 304-308.
Amzica, "Physiology of Sleep and Wakefulness as it Relates to the Physiology of Epilepsy," Journal of Clinical Neurophysiology, American Clinical Neurophysiology Society, 19(6), Dec. 2002, pp. 488-503.
Antonini et al., "Deep brain stimulation and its effect on sleep in Parkinson's disease," Sleep Medicine, vol. 5, Issue 2, Mar. 2004, pp. 211-214.
Cicolin et al., "Effects of deep brain stimulation of the subthalamic nucleus on sleep architecture in parkinsonian patients," Sleep Medicine, vol. 5, Issue 2, Mar. 2004, pp. 207-210.
Criticare System Inc., —504DX Portable Pulse Oximeter, http://www.csiusa.com/504dx.html, Jan. 31, 2005, 4 pp.
Dinner, "Effect of Sleep of Epilepsy," Journal of Clinical Neurophysiology, American Clinical Neurophysiology Society, 19(6), Dec. 2002, pp. 504-513.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Societ, 19(6), Dec. 2002, pp. 514-521.
Goodrich et al., "The Prediction of Pain Using Measures of Sleep Quality," Pain Digest, 8, 1998, pp. 23-25 (Applicant points out that, in accordance with MPEP 609.04(a), the 1998 year of publication is sufficiently earlier than the effective U.S. filed and any foreign priority date of Mar. 16, 2004 so that the particular month of publication is not in issue.).
Greenberg, MD, Phd. et al., "Mechanisms and the current state of deep brain stimulation in neuropsychiatry," CNS Spectrums, vol. 8, No. 7, Jul. 2003, pp. 522-526.
Itamar Medical Information, http://itamar-medical.com/content.asp?id=31, Jan. 31, 2005, 2 pp.
Kassam, "2005 EDP Topic 'MK4': Tremor Data-Logger for Parkinson's Disease Patients," http://www.ee.ryerson.ca/~courses/edp2005/MK4.html, Feb. 20, 2006, 3 pp.
Kerr et al., "Analysis of the sit-stand-sit movement cycle in normal subjects," Clinical Bimechanics, vol. 12, No. 4, Jun. 1997, pp. 236-245.
MAP Medizin—Technologie GmbH, Poly-MESAM®, http://195.244.124.130/map/de/eng/map_med.nsf/cmsall/705643A3FCBE4188AC1256EF4 . . . , Jan. 31, 2005, 4 pp.
Medcare—A Global Leader in Sleep Diagnostics, Embletta Recording System, http://www.medcare.com/products/diagnostic/embletta/, Jan. 31, 2005, 2 pp.
Medcare—A Global Leader in Sleep Diagnostics, Somnologica for Embeltta, http://www.medcare.com/products/diagnostic/embletta/SomnoEmbletta/index.asp, Jan. 31,2005, 1 pp.
Mendez et al., "Interactions Between Sleep and Epilepsy," Journal of Clinical Neurophysiology American Clinical Neurophysiology Society, 18(2), Mar. 2001, pp. 106-127.
Merlin, http://www.aha.ru/~pir/english/merlin, Jan. 31, 2005, 4 pp.
Oerlemans et al., "The prevalence of sleep disorders in patients with Parkinson's disease. A self-reported, community-based survey," Sleep Medicine, vol. 3, Issue 2, Mar. 2002, pp. 147-149.

Sleep Solutions—PR Newsire: Sleep Solutions Introduces NovaSom™ OSG™ for PSG . . . , http://www.sleep-solutions.com/press_room/novasom.htm, Jan. 31, 2005, 2 pp.
Sleep Strip & Bite Strip, http://www.quietsleep.com/snoringapnea/sleepstrip.htm, Jan. 31, 2005, 7 pp.
Smith, et al., "How do sleep disturbance and chronic pain interrelate? Insights form the longitudinal and cognitive-behavioral clinical trials literature," Sleep Medicine Reviews, YSMRV 286, Jun. 19, 2003, 14 pp.
Smith, et al., "Presleep Cognitions in Patients with Insomnia Secondary to Chronic Pain," Journal of Behavioral Medicine, vol. 24, No. 1, Feb. 2001, pp. 93-114.
Snap® Laboratories, Product Fact Sheet, http://www.snaplab.com/mp_fact.htm, Jan. 31, 2005, 2 pp.
Tuisku, "Motor Activity Measured by Actometry in Neuropsychiatric Disorders," Department of Psychiatry, University of Helsinski, Helsinki, Finland, Dec. 13, 2002, 115 pp.
Van Dam et al., "Measuring physical activity in patients after surgery for a malignant tumour in the leg," The Journal of Bone & Joint Surgery, vol. 83-B, No. 7, Sep. 2001, pp. 1015-1019.
Prosecution History from U.S. Appl. No. 11/081,857, from Nov. 13, 2007 through Jan. 12, 2010, 107 pp.
Prosecution History from U.S. Appl. No. 11/691,425, from Nov. 8, 2011 through Jul. 9, 2012, 71 pp.
Prosecution History from U.S. Appl. No. 11/081,873, from Nov. 7, 2007 through Jul. 9, 2008, 48 pp.
Prosecution History from U.S. Appl. No. 11/691,413, from Mar. 12, 2010 through May 17, 2011, 64 pp.
Prosecution History from U.S. Appl. No. 12/248,622, from May 20, 2010 through Jan. 20, 2012, 78 pp.
Prosecution History from U.S. Appl. No. 12/248,609, from Aug. 5, 2010 through Jan. 19, 2012, 78 pp.
Prosecution History from U.S. Appl. No. 10/825,965, from Jun. 9, 2006 through Feb. 28, 2008, 89 pp.
Prosecution History from U.S. Appl. No. 11/081,785, from Jan. 10, 2006 through Sep. 7, 2006, 35 pp.
Prosecution History from U.S. Appl. No. 11/691,411, from Jan. 12, 2010 through May 19, 2010, 27 pp.
Prosecution History from U.S. Appl. No. 11/691,423, from Apr. 22, 2010 through Jan. 29, 2014, 52 pp.
Prosecution History from U.S. Appl. No. 11/796,811, from Apr. 23, 2008 through Aug. 17, 2009, 51 pp.
Prosecution History from U.S. Appl. No. 12/017,918, from May 6, 2010 through Jan. 25, 2011, 38 pp.
Prosecution History from U.S. Appl. No. 12/498,928, from Aug. 1, 2011 through Feb. 1, 2012, 24 pp.
Prosecution History from U.S. Appl. No. 14/278,821, from Nov. 17, 2015 through Nov. 1, 2016, 40 pp.
Singh et al.,"Freezing of Gait-Related Oscillatory Activity in the Human Subthalamic Nucleus," Basal Ganglia, vol. 3, No. 1, Mar. 1, 2013, pp. 25-32.
Ricchi et al., "Transient Effects of 80 Hz Stimulation on Gait in STN-DBS Treated PD Patients: A 15 Months Follow-Up Study," Brain Stimulation, vol. 5, No. 3, Jul. 1, 2012, pp. 388-392.
Toledo et al., "High-Beta Activity in the Subthalmic Nucleus and Freezing of Gait in Parkinson's Disease," Neurobiology of Disease, vol. 64, Jan. 1, 2014, pp. 60-65.
Rechtschaffen, et al., "A manual of standardized terminology, techniques and scoring system for sleep stages of Human subjects," Public Health Service, U.S. Government Printing Office, 1968 (reprinted 1971), 59 pages (Applicant points out, in accordance with MPEP 609.04(a), that the year of publication, 1968, is sufficiently earlier than the effective U.S. filing dated, Feb. 22, 2017, so that the particular month of publication is not in issue.).
Gennaro, et al., "Sleep spindles: an overview," Sleep Medicine Reviews, vol. 7, No. 5, pp. 423-440, Oct. 2003.
U.S. Appl. No. 15/664,798, filed by Jianping Wu, et al., filed Jul. 31, 2017, 37 pp.

| PARAMETER SET | PARAMETERS | % OF TIME ACTIVE | COUNTS/HOUR |
|---|---|---|---|
| 1 | PA = 5.5V<br>PW = 210ms<br>PR = 90Hz | 75%<br>(15% HIGH) | 100 |
| 2 | PA = 5V<br>PW = 190ms<br>PR = 95Hz | 60%<br>(5% HIGH) | 67 |
| ••• | | | |
| N | PA = 4.6V<br>PW = 215ms<br>PR = 80Hz | 55%<br>(8% HIGH) | 72 |

FIG. 7

| PARAMETER SET | PARAMETERS | GAIT REGULARITY | GAIT FREEZE/DAY |
|---|---|---|---|
| 1 | PA = 5.5V<br>PW = 210ms<br>PR = 90Hz | 0.90 | 2 |
| 2 | PA = 5V<br>PW = 190ms<br>PR = 95Hz | 0.75 | 1.2 |
| ••• | | | |
| N | PA = 4.6V<br>PW = 215ms<br>PR = 80Hz | 0.76 | 4 |

FIG. 12

COLLECTING GAIT INFORMATION FOR EVALUATION AND CONTROL OF THERAPY

This application is a continuation of U.S. patent application Ser. No. 14/278,821, filed May 15, 2014, which issued as U.S. Pat. No. 9,592,379 on Mar. 14, 2017, which is a continuation of U.S. patent application Ser. No. 11/691,423, filed Mar. 26, 2007, which issued as U.S. Pat. No. 8,744,587 on Jul. 3, 2014, which claims the benefit of U.S. Provisional Application No. 60/785,658, filed Mar. 24, 2006. The entire content of each of these applications is incorporated by reference herein.

TECHNICAL FIELD

The invention relates to medical devices and, more particularly, to medical devices that deliver therapy.

BACKGROUND

In some cases, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement or neurological disorders, such as tremor or Parkinson's disease, which may result in irregular movement or activity, as well as a generally decreased level of activity. Further, other neurological disorders may affect a patient's physical activity. For example, epilepsy is an example of a neurological disorder that may change or otherwise affect physical activity frequency or magnitude of the patient. Occurring epileptic seizures, or the threat of seizures, may deter physical activity. Additional neurological disorders may include tremor, multiple sclerosis, or spasticity.

Neurological disorders may also include other disorders. The difficulty walking or otherwise moving experienced by patients with movement disorders may cause such patients to avoid movement to the extent possible. Further, mood or other psychological disorders, congestive heart failure, or cardiac arrhythmia are other examples of disorders that may generally cause a patient to be less active.

Drugs are often used to treat neurological disorders. In some cases, these ailments are treated via a medical device, such as an implantable medical device (IMD). For example, patients may receive an implantable neurostimulator or drug delivery device to treat chronic pain, a movement disorder, a neurological disorder, or a mood disorder. Congestive heart failure and arrhythmia may be treated by, for example, a cardiac pacemaker or drug delivery device.

SUMMARY

In general, the invention is directed to techniques for evaluating a therapy delivered to a patient by a medical device based on patient activity. More specifically, patient activity and/or gait may be detected and used to evaluate or control delivery of therapy for patients with movement disorders, such as Parkinson's disease. At any given time, the medical device delivers the therapy according to a current set of therapy parameters. The therapy parameters may change over time such that the therapy is delivered according to a plurality of different therapy parameter sets. The medical device, or another device, periodically determines an activity level of the patient, and associates each determined activity level with the current therapy parameter set.

An activity signal monitored according to embodiments the invention may be indicative of patient gait in order to identify gait irregularity and/or gait freeze events. A value of at least one activity metric is determined for each of the therapy parameter sets based on the activity levels and/or gait parameters associated with that parameter set. For example, gait parameters may be monitored with accelerometers or other sensors capable of measuring the gait of the patient.

A list of the therapy parameter sets and associated activity metrics is presented to a user, such as a clinician, for evaluation of the relative efficacy of the therapy parameter sets. The list may be ordered according to the activity metric values to aid in evaluation of the therapy parameter sets. In this manner, the user may readily identify the therapy parameter sets that support the highest activity levels for the patient or reduce or eliminate gait irregularity or freeze of the patient, and thereby evaluate the relative efficacy of the parameter sets.

The therapy may be directed to treating any number of disorders. For example, the therapy may be directed to treating a non-respiratory neurological disorder, such as a movement disorder or psychological disorder. Example movement disorders for which therapy may be provided are Parkinson's disease, essential tremor and epilepsy. Non-respiratory neurological disorders do not include respiratory disorders, such as sleep apnea.

The therapy delivering medical device or another device may monitor at least one signal that is generated by a sensor and varies as a function of patient activity. For example, the device may monitor a signal generated by an accelerometer, a bonded piezoelectric crystal, a mercury switch, or a gyro. In some embodiments, the device may monitor a signal that indicates a physiological parameter of the patient, which in turn varies as a function of patient activity. For example, the device may monitor a signal that indicates the heart rate, electrocardiogram (ECG) morphology, electroencephalogram (EEG) morphology, respiration rate, respiratory volume, core temperature, subcutaneous temperature, or muscular activity of the patient.

The therapy delivering medical device or another device may periodically determine an activity level of the patient based on the one or more signals. In some embodiments, the device periodically determines a number of activity counts based on the signals, and the number of activity counts is stored as the activity level. The number of activity counts may be a number of threshold crossings by a signal generated by a sensor such as an accelerometer or piezoelectric crystal during a sample period, or a number of switch contacts indicated by the signal generated by a sensor such as mercury switch during a sample period.

In some embodiments, the device may periodically determine a heart rate, measured value of one or more ECG morphological features, EEG signals, respiration rate, respiratory volume, core temperature, subcutaneous temperature, and/or muscular activity level of the patient based on one or more signals. The determined values of these parameters may be mean or median values. The device may compare a determined value of such a physiological parameter to one or more thresholds to determine a number of activity counts, which may be stored as a determined activity level. In other embodiments, the device may store the determined physiological parameter value as a determined activity level.

The use of activity counts, however, may allow the device to determine an activity level based on a plurality of signals. For example, the device may determine a first number of activity counts based on an accelerometer signal and a second number of activity counts based on a heart rate determined at the time the accelerometer signal was sampled. The device may determine an activity level by calculating the sum or average, which may be a weighted sum or average, of first and second activity counts.

As mentioned above, the device may associate each determined activity level with a current set of therapy parameters and, for each of a plurality of therapy parameter sets used by the medical device over time, a value of one or more activity metrics is determined. An activity metric value may be, for example, a mean or median activity level, such as an average number of activity counts per unit time. In other embodiments, an activity metric value may be chosen from a predetermined scale of activity metric values based on comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set. One or both of the medical device or another device, such as a programming device or other computing device, may determine the activity metric values as described herein.

Further, in some embodiments, activity levels or activity sensor signals may be compared to thresholds or templates, or otherwise analyzed, to determine the regularity of gait or identify the occurrence of a gait freeze event. In such embodiments, activity sensor signals may include signals that reflect gross anatomical movement, muscle activity, or footfalls of the patient, such as accelerometer signals or piezoelectric crystal signals. A value indicative of the regularity of the gait may be determined, and associated with a therapy parameter set that was currently being used to control delivery of therapy when the gait regularity value was determined. When a gait freeze event is identified, the occurrence of a gait freeze event may be associated with a therapy parameter set that was current being used to control delivery of therapy when the gait freeze event occurred.

The computing device or, in some external medical device embodiments, the medical device, presents a list of the plurality of parameter sets, associated activity metric values, such as gait regularity or a number gait freeze events, via a display. The computing device may order the list according to the activity metric values. Where values are determined for a plurality of activity metrics for each of the therapy parameter sets, the computing device may order the list according to the values of a user selected one of the activity metrics. The computing device may also present other activity information to a user, such as a trend diagram of activity, gait regularity, or gait freeze events over time, or a histogram or pie chart illustrating percentages of time that activity levels were within certain ranges. The computing device may generate such charts or diagrams using activity levels associated with a particular one of the therapy parameter sets, or all of the determined activity levels.

In one embodiment, the invention is directed to a method that includes delivering a therapy from a medical device to a patient to treat a movement disorder, monitoring gait of the patient based on a signal generated by a sensor that varies as a function of patient activity and, for each of a plurality of therapy parameter sets used by the medical device to control delivery of the therapy to the patient, determining a value of at least one metric based on the gait of the patient during delivery of the therapy by the medical device according to the therapy parameter set.

In another embodiment, the invention is directed to a system that includes a medical device that delivers at least one of a movement disorder therapy, Parkinson's disease therapy, epilepsy therapy, tremor therapy, or deep brain stimulation to a patient. The system further comprises an implanted sensor that generates a signal that varies as a function of activity of the patient, and a processor. The processor monitors gait of the patient based on the signal and, for each of a plurality of therapy parameter sets used by the medical device to control delivery of the therapy to the patient, determines a value of at least one metric based on the gait of the patient during delivery of the therapy by the medical device according to the therapy parameter set.

In another embodiment, the invention is directed to a computer-readable medium including instructions that cause a processor to monitor gait of a patient based on a signal generated by a sensor that varies as a function of patient activity and, for each of a plurality of therapy parameter sets used by a medical device to control delivery of a therapy to the patient, determine a value of at least one metric based on the gait of the patient during delivery of the therapy by the medical device according to the therapy parameter set, wherein the therapy comprises at least one of a movement disorder therapy, Parkinson's disease therapy, epilepsy therapy, tremor therapy, or deep brain stimulation.

In another embodiment, the invention is directed to a method that includes delivering a therapy from an implantable medical device to a patient to treat a movement disorder, monitoring gait of the patient with the implantable medical device based on a signal generated by a sensor that varies as a function of patient activity, and detecting a gait freeze event with the implantable medical device based on the signal.

In another embodiment, the invention is directed to a system comprising an implantable medical device that delivers at least one of a movement disorder therapy, Parkinson's disease therapy, epilepsy therapy, tremor therapy, or deep brain stimulation to a patient. The system further comprises an implanted sensor that generates a signal that varies as a function of activity of the patient, and a processor that monitors gait of the patient based on the signal, and detects a gait freeze event based on the signal.

The invention is capable of providing one or more advantages. For example, a medical system according to the invention may provide a clinician with an objective indication of the efficacy of different sets of therapy parameters to improve gait or reduce the frequency of gait freeze events in patients with Parkinson's disease. Further, by displaying therapy parameter sets and associated activity metric values in an ordered and, in some cases, sortable list, the medical system may allow the clinician to more easily compare the relative efficacies of a plurality of therapy parameter sets. The medical system may be particularly useful in the context of trial neurostimulation or drug delivery, where the patient is encouraged to try a plurality of therapy parameter sets to allow the patient and clinician to identify efficacious therapy parameter sets. Further, the medical system may be particularly useful in the context of movement disorders, which may impact both the overall level of patient activity, and also result in irregular movements with activity.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 7 illustrates an example list of therapy parameter sets and associated activity metric values that may be presented by a clinician programmer.

FIG. 12 illustrates an example list of therapy parameter sets and associated activity metric values relating to patient gait which may be presented by a clinician programmer.

DETAILED DESCRIPTION

Figure 1A:
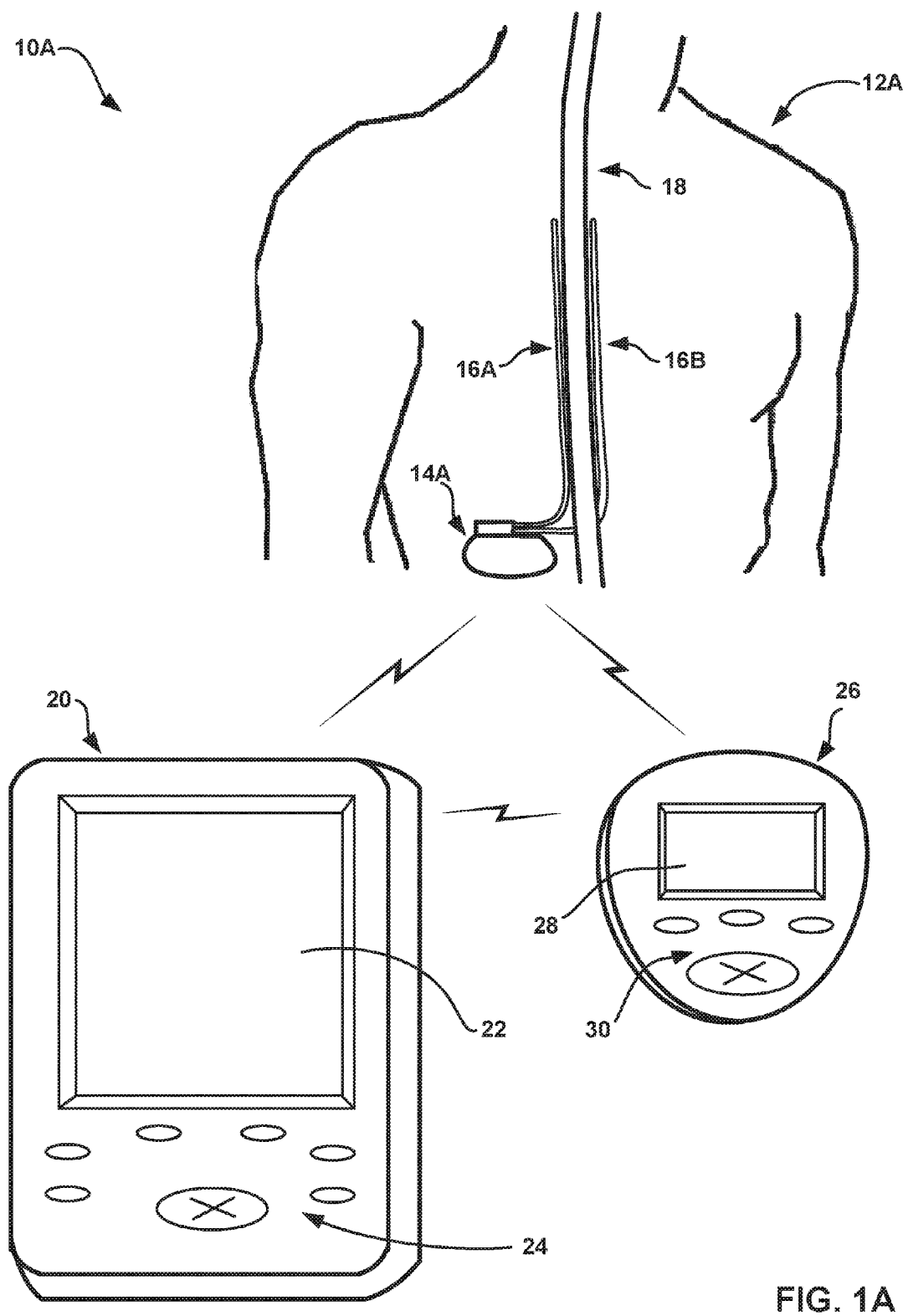
FIGS. 1A and 1B are conceptual diagrams illustrating example systems that include an implantable medical device that collects activity information according to the invention.
Figure 1B:
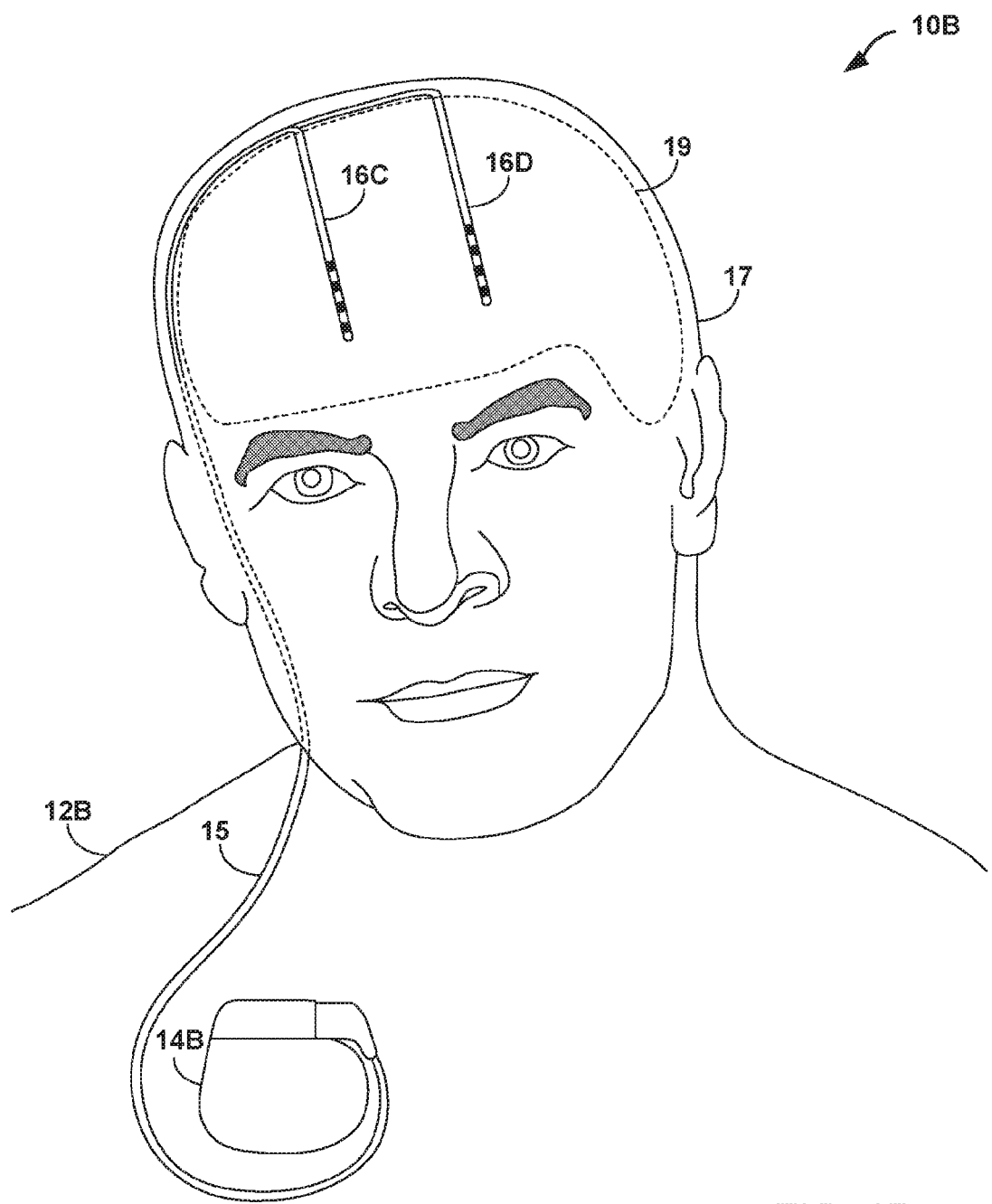

FIGS. 1A and 1B are conceptual diagrams illustrating example systems 10A and 10B (collectively "systems 10") that respectively include an implantable medical device (IMD) 14A or 14B (collectively "IMDs 14") that collect information relating to the activity of a respective one of patients 12A and 12 B (collectively "patients 12"). In the illustrated example systems 10, IMDs 14 take the form of an implantable neurostimulator that delivers neurostimulation therapy in the form of electrical pulses to patients 12. However, the invention is not limited to implementation via an implantable neurostimulators. For example, in some embodiments of the invention, IMD 14 may take the form of an implantable pump or implantable cardiac rhythm management device, such as a pacemaker, that collects activity information. Further, the invention is not limited to implementation via an IMD. In other words, any implantable or external device may collect activity information according to the invention.

In the illustrated examples of FIGS. 1A and 1B, IMDs 14A and 14B respectively deliver neurostimulation therapy to patients 12A and 12B via leads 16A and 16B, and leads 16C and 16D (collectively "leads 16"), respectively. Leads 16A and 16B may, as shown in FIG. 1A, be implanted proximate to the spinal cord 18 of patient 12A, and IMD 14A may deliver spinal cord stimulation (SCS) therapy to patient 12A in order to, for example, reduce pain experienced by patient 12A. However, the invention is not limited to the configuration of leads 16A and 16B shown in FIG. 1A or the delivery of SCS or other pain therapies.

For example, in another embodiment, illustrated in FIG. 1B, leads 16C and 16D may extend to brain 19 of patient 12B, e.g., through cranium 17 of patient. IMD 14B may deliver deep brain stimulation (DBS) or cortical stimulation therapy to patient 12 to treat any of a variety of non-respiratory neurological disorders, such as movement disorders or psychological disorders. Example therapies may treat tremor, Parkinson's disease, spasticity, epilepsy, depression or obsessive-compulsive disorder. As illustrated in FIG. 1B, leads 16C and 16D may be coupled to IMD 14B via one or more lead extensions 15. Leads 16C and 16D may be placed within the brain of patient 12B according to commonly used DBS applications.

As further examples, one or more leads 16 may be implanted proximate to the pelvic nerves (not shown) or stomach (not shown), and an IMD 14 may deliver neurostimulation therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

The illustrated numbers and locations of leads 16 are merely examples. Embodiments of the invention may include any number of lead implanted at any of a variety of locations within a patient. Furthermore, the illustrated number and location of IMDs 14 are merely examples. IMDs 14 may be located anywhere within patient according to various embodiments of the invention. For example, in some embodiments, an IMD 14 may be implanted on or within cranium 17 for delivery of therapy to brain 19, or other structure of the head of the patient 12.

IMDs 14 deliver therapy according to a set of therapy parameters, i.e., a set of values for a number of parameters that define the therapy delivered according to that therapy parameter set. In embodiments where IMDs 14 deliver neurostimulation therapy in the form of electrical pulses, the parameters for each therapy parameter set may include voltage or current pulse amplitudes, pulse widths, pulse rates, duration, duty cycle and the like. Further, each of leads 16 includes electrodes (not shown in FIGS. 1A and 1B), and a therapy parameter set may include information identifying which electrodes have been selected for delivery of pulses, and the polarities of the selected electrodes. In embodiments in which IMDs 14 deliver other types of therapies, therapy parameter sets may include other therapy parameters, such as drug concentration and drug flow rate in the case of drug delivery therapy. Therapy parameter sets used by IMDs 14 may include a number of parameter sets programmed by one or more clinicians (not shown), and parameter sets representing adjustments made by patients 12 to these preprogrammed sets.

IMDs 14 may deliver electrical stimulation to treat and/or reduce the symptoms of any of a variety of non-respiratory neurological disorders (hereinafter referred to as only "neurological disorders"). These neurological disorders may not include respiratory disorders, such as central sleep apnea. For example, IMD 14B may deliver DBS in order to, for example, reduce the frequency and severity of epileptic seizures experienced by patient 12B with epilepsy. As other examples, IMD 14B may deliver DBS in order to reduce the symptoms of a movement disorder or psychological disorder, such as tremor, Parkinson's disease, multiple sclerosis, spasticity, depression, mania, bipolar disorder, or obsessive-compulsive disorder. Additionally, IMD 14A may deliver SCS, or IMD 14B may deliver DBS to treat chronic pain or other non-respiratory neurological disorders, e.g., excluding for example central sleep apnea.

Each of systems 10 may also include a clinician programmer 20 (illustrated as part of system 10A in FIG. 1A). The clinician may use clinician programmer 20 to program therapy for patient 12A, e.g., specify a number of therapy parameter sets and provide the parameter sets to IMD 14A. The clinician may also use clinician programmer 20 to retrieve information collected by IMD 14A. The clinician may use clinician programmer 20 to communicate with IMD 14A both during initial programming of IMD 14A, and for collection of information and further programming during follow-up visits.

Clinician programmer 20 may, as shown in FIG. 1A, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

Systems 10 may also include a patient programmer 26 (illustrated as part of system 10A in FIG. 1A), which also may, as shown in FIG. 1A, be a handheld computing device. Patient 12A may use patient programmer 26 to control the delivery of therapy by IMD 14A. For example, using patient programmer 26, patient 12A may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12A to interact with patient programmer 26. In some embodiments, display 28 may be a touch screen display, and patient 12A may interact with patient programmer 26 via display 28. Patient 12A may also interact with patient programmer 26 using peripheral pointing devices, such as a stylus, mouse, or the like.

Clinician and patient programmers 20, 26 are not limited to the hand-held computer embodiments illustrated in FIG. 1A. Programmers 20, 26 according to the invention may be any sort of computing device. For example, a programmer 20, 26 according to the invention may be a tablet-based computing device, a desktop computing device, or a workstation.

IMDs 14, clinician programmers 20 and patient programmers 26 may, as shown in FIG. 1A, communicate via wireless communication. Clinician programmer 20 and patient programmer 26 may, for example, communicate via wireless communication with IMD 14A using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMDs 14 collect patient activity information. Specifically, as will be described in greater detail below, IMDs 14 may periodically determine an activity level of patient 12 based on a signal that varies as a function of patient activity. IMDs 14 may associate each determined activity level with the therapy parameter set that is currently active when the activity level is determined. An activity level may comprise, for example, a number of activity counts, or a value for a physiological parameter that reflects patient activity.

Over time, IMDs 14 use a plurality of therapy parameter sets to deliver the therapy to patient 12. A processor within IMDs 14 or another device, such as one of programmers 20, 26 or another computing device, determines a value of one or more activity metrics for each of the plurality of therapy parameter sets based on the activity levels associated with the therapy parameter sets. An activity metric value may be, for example, a mean or median activity level, such as an average number of activity counts per unit time. In other embodiments, an activity metric value may be chosen from a predetermined scale of activity metric values based on a comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set.

Furthermore, in some embodiments, gait regularity or a number of gait freeze events occurring during delivery of therapy according to a parameter set may be an activity metric value for the therapy parameter set. In some embodiments, activity levels or activity sensor signals may be compared to thresholds or templates, or otherwise analyzed, to determine gait regularity or identify the occurrence of a gait freeze event. In such embodiments, activity sensor signals may include signals that reflect gross anatomical movement, muscle activity, or footfalls of the patient, such accelerometer signals or piezoelectric crystal signals. A value indicative of the regularity of the gait may be determined, and associated with a therapy parameter set that was currently being used to control delivery of therapy when the gait regularity value was determined. When a gait freeze event is identified, the occurrence of a gait freeze event may be associated with a therapy parameter sets that was current being used to control delivery of therapy when the gait freeze event occurred.

In some embodiments, a plurality of activity metric values are determined for each of the plurality of therapy parameter sets. In such embodiments, an overall activity metric value may be determined. For example, the plurality of individual activity metric values may be used as indices to identify an overall activity metric value from a look-up table. The overall activity metric may be selected from a predetermined scale of activity metric values, which may be numeric, such as activity metric values from 1-10, or qualitative, such as low, medium or high activity.

One or more of IMDs 14, programmers 20, 26, or another computing device may determine the activity metric values as described herein. In some embodiments, IMDs 14 determine and store activity metric values for each of a plurality of therapy parameter sets, and provide information identifying the therapy parameter sets and the associated activity metric values to clinician programmers 20. In other embodiments, IMDs 14 provide information identifying the therapy parameter sets and associated activity levels or signals to clinician programmers 20, and clinician programmers 20 determines the activity metric values for each of the therapy parameter sets.

In either of these embodiments, clinician programmers 20 present a list of the plurality of parameter sets and associated activity metric values to the clinician via display 22. Programmers 20 may order the list according to the activity metric values. Where values are determined for a plurality of activity metrics for each of the therapy parameter sets, programmers 20 may order the list according to the values of one of the activity metrics that is selected by the clinician. Programmers 20 may also present other activity information to the clinician, such as a trend diagram of activity over time, or a histogram or pie chart illustrating percentages of time that activity levels were within certain ranges. Programmers 20 may generate such charts or diagrams using activity levels associated with a particular one of the therapy parameter sets, or all of the activity levels determined by IMDs 14.

However, the invention is not limited to embodiments that include programmers 20, or embodiments in which programmers 20 presents activity information to the clinician. For example, in some embodiments, programmers 26 present activity information as described herein to one or both of the clinician and patients 12. Further, in some embodiments, an external medical device comprises a display. In such embodiments, the external medical device may both determine activity metric values for the plurality of therapy parameter sets, and present the list of therapy parameter sets and activity metric values. Additionally, in some embodiments, any type of computing device, e.g., personal computer, workstation, or server, may identify activity levels, determine activity metric values, and/or present a list to a patient or clinician.

Further, the invention is not limited to embodiments in which a medical device collects activity signals or determines activity levels. For example, in some embodiments, IMDs 14 may instead periodically record samples of one or more signals that vary as a function of patient activity, and associate the samples with a current therapy parameter set. In such embodiments, programmers 20 or 26, or another computing device, may receive information identifying a plurality of therapy parameter sets and the samples associated with the parameter sets, may determine activity levels and/or metric values based on the samples.

Figure 2A:
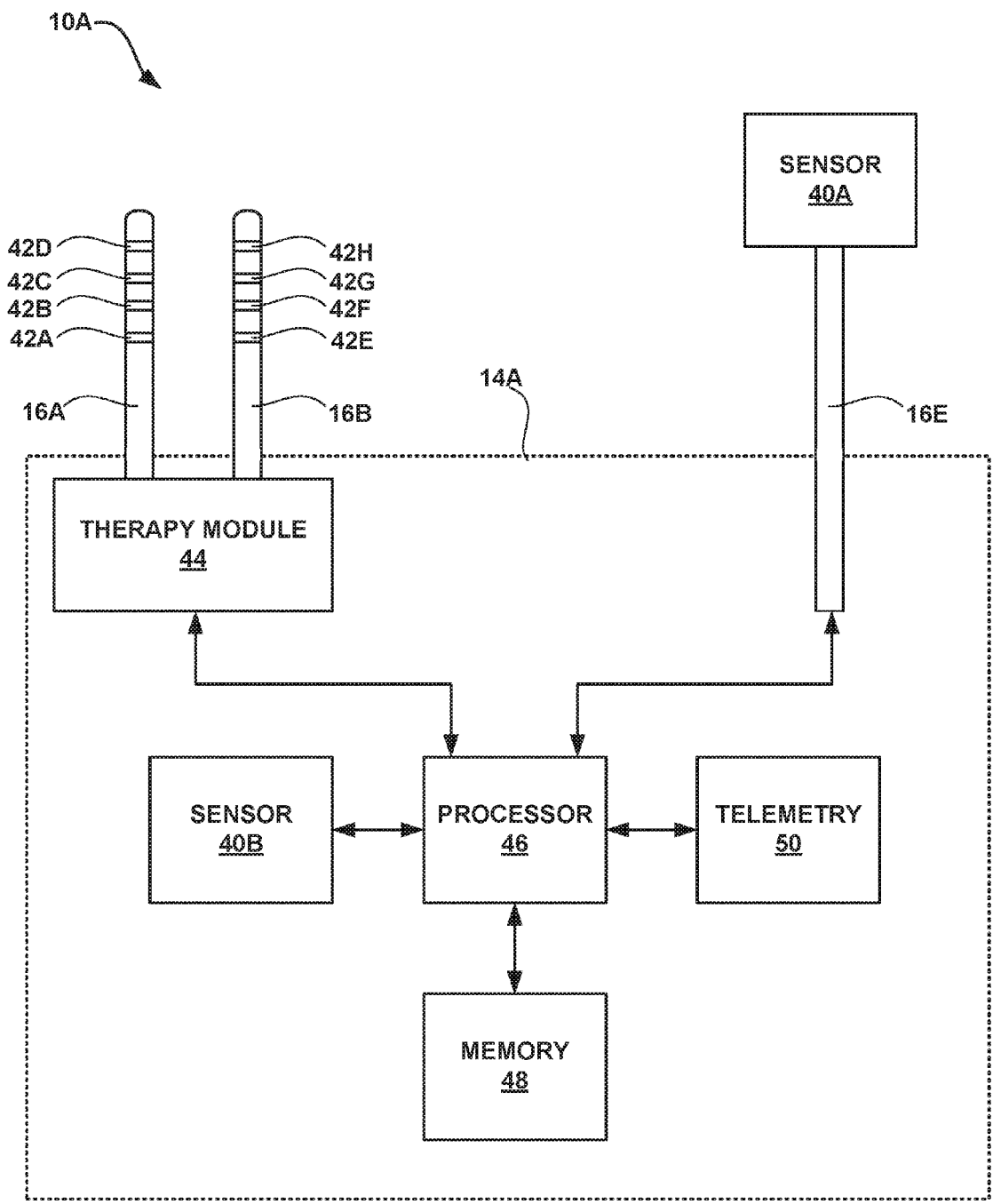
FIGS. 2A and 2B are block diagrams further illustrating the example systems and implantable medical devices of FIGS. 1A and 1B.
Figure 2B:
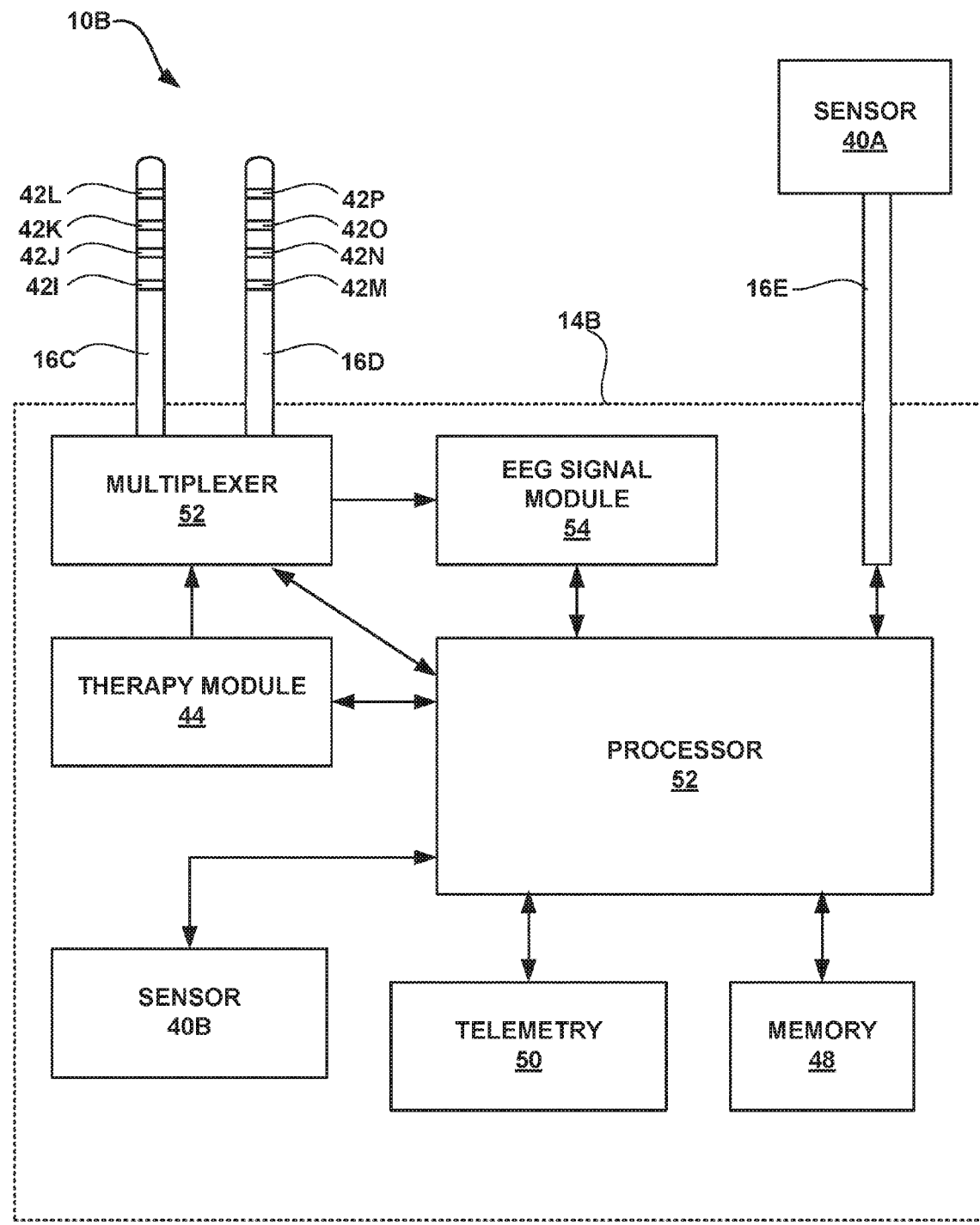

FIGS. 2A and 2B are block diagrams further illustrating systems 10A and 10B. In particular, FIG. 2A illustrates an example configuration of IMD 14A and leads 16A and 16B. FIG. 2B illustrates an example configuration of IMD 14B and leads 16C and 16D. FIGS. 2A and 2B also illustrate sensors 40A and 40B (collectively "sensors 40") that generate signals that vary as a function of patient activity. As will be described in greater detail below, IMDs 14 monitor the signals, and may periodically determine an activity level or gait parameter, or identify a gait freeze event, based on the signals.

IMDs 14 may deliver neurostimulation therapy via electrodes 42A-D of lead 16A and electrodes 42E-H of lead 16B, while IMD 14B delivers neurostimulation via electrodes 42I-L of lead 16C and electrodes 42 M-P of lead 16D (collectively "electrodes 42"). Electrodes 42 may be ring electrodes. The configuration, type and number of electrodes 42 illustrated in FIGS. 2A and 2B are merely exemplary. For example, leads 16 may each include eight electrodes 42, and the electrodes 42 need not be arranged linearly on each of leads 16.

In each of systems 10A and 10B, electrodes 42 are electrically coupled to a therapy delivery module 44 via leads 16. Therapy delivery module 44 may, for example, include an output pulse generator coupled to a power source such as a battery. Therapy delivery module 44 may deliver electrical pulses to a patient 12 via at least some of electrodes 42 under the control of a processor 46, which controls therapy delivery module 44 to deliver neurostimulation therapy according to a current therapy parameter set. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal that varies as a function of a patient 12 activity. IMDs 14 may include circuitry (not shown) that conditions the signals generated by sensors 40 such that they may be analyzed by processor 46. For example, IMDs 14 may include one or more analog to digital converters to convert analog signals generated by sensors 40 into digital signals usable by processor 46, as well as suitable filter and amplifier circuitry. Although shown as including two sensors 40, systems 10A and 10B may include any number of sensors.

Further, as illustrated in FIGS. 2A and 2B, sensors 40 may be included as part of IMDs 14, or coupled to IMDs 14 via leads 16. Sensors 40 may be coupled to IMD 14 via therapy leads 16A-16D, or via other leads 16, such as lead 16E depicted in FIGS. 2A and 2B. In some embodiments, a sensor 40 located outside of an IMD 14 may be in wireless communication with processor 46. Wireless communication between sensors 40 and IMDs 14 may, as examples, include RF communication or communication via electrical signals conducted through the tissue and/or fluid of a patient 12.

A sensor 40 may be, for example, an accelerometer, a bonded piezoelectric crystal, a mercury switch, or a gyro that generates a signal as a function of patient activity, e.g., body motion, footfalls or other impact events, and the like. Processor 46 may determine an activity level based on a signal generated by one of these types of sensors 40 by sampling the signal and determining a number of activity counts during the sample period. Processor 46 may then store the determined number of activity counts in memory 48 as an activity level.

For example, processor 46 may compare the sample of a signal generated by an accelerometer or piezoelectric crystal to one or more amplitude thresholds stored within memory 48. Processor 46 may identify each threshold crossing as an activity count. Where processor 46 compares the sample to multiple thresholds with varying amplitudes, processor 46 may identify crossing of higher amplitude thresholds as multiple activity counts. Using multiple thresholds to identify activity counts, processor 46 may be able to more accurately determine the extent of patient activity for both high impact, low frequency and low impact, high frequency activities. In embodiments in which a sensor 40 takes the form of a mercury switch, processor 46 may identify the number of switch contacts indicated during the sample period as the number of activity counts.

In embodiments in which a sensor 40 comprises an accelerometer or piezoelectric crystal, IMDs 14 may include a filter (not shown), or processor 46 may apply a digital filter, that passes a band from approximately 0.1 Hz to 10 Hz. The filter may reduce noise in the signal, and pass the portion of the signal that reflects patient activity.

In some embodiments, sensors 40 may generate a signal both as a function of patient activity and patient posture. For example, accelerometers, gyros, or magnetometers may generate signals that indicate both the activity and the posture of a patient 12. As will be described below, posture may be monitored to confirm a specific activity event, gait freeze, as will be discussed in greater detail below.

In some embodiments, in order to identify posture, sensors 40 such as accelerometers may be oriented substantially orthogonally with respect to each other. In addition to being oriented orthogonally with respect to each other, each of sensors 40 used to detect the posture of a patient 12 may be substantially aligned with an axis of the body of a patient 12. When accelerometers, for example, are aligned in this manner, the magnitude and polarity of DC components of the signals generate by the accelerometers indicate the orientation of the patient relative to the Earth's gravity, e.g., the posture of a patient 12. Further information regarding use of orthogonally aligned accelerometers to determine patient posture may be found in a commonly assigned U.S. Pat. No. 5,593,431, which issued to Todd J. Sheldon.

Other sensors 40 that may generate a signal that indicates the posture of a patient 12 include electrodes that generate a signal as a function of electrical activity within muscles of a patient 12, e.g., an electromyogram (EMG) signal, or a bonded piezoelectric crystal that generates a signal as a function of contraction of muscles. Electrodes or bonded piezoelectric crystals may be implanted in the legs, buttocks, chest, abdomen, or back of a patient 12, and coupled to IMDs 14 wirelessly or via one or more leads 16. Alternatively, electrodes may be integrated in a housing of the IMD or piezoelectric crystals may be bonded to the housing when IMD is implanted in the buttocks, chest, abdomen, or back of a patient 12. The signals generated by such sensors when implanted in these locations may vary based on the posture of a patient 12, e.g., may vary based on whether the patient is standing, sitting, or lying down.

Further, the posture of a patient 12 may affect the thoracic impedance of the patient. Consequently, sensors 40 may include an electrode pair, including one electrode integrated with the housing of IMDs 14 and one of electrodes 42, that generates a signal as a function of the thoracic impedance of a patient 12, and processor 46 may detect the posture or posture changes of a patient 12 based on the signal. The electrodes of the pair may be located on opposite sides of the patient's thorax. For example, the electrode pair may include one of electrodes 42 located proximate to the spine of a patient for delivery of SCS therapy, and IMD 14A with an electrode integrated in its housing may be implanted in the abdomen or chest of patient 12A. As another example, IMD 14B may include electrodes implanted to detect thoracic impedance in addition to leads 16 implanted within the brain of patient 12B. The posture or posture changes may affect the delivery of DBS or SCS therapy to either patient 12A or 12B for the treatment of any type of neurological disorder, and may also be used to detect patient sleep, as described herein.

Additionally, changes of the posture of a patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to IMDs 14 wirelessly or via one of leads 16. CSF pressure changes associated with posture changes may be particularly evident within the brain of the patient, e.g., may be particularly apparent in an intracranial pressure (ICP) waveform.

In some embodiments, processor 46 may monitor a signal that indicates a physiological parameter of a patient 12, which in turn varies as a function of patient activity. For example, processor 46 may monitor a signal that indicates the heart rate, ECG morphology, EEG morphology, respiration rate, respiratory volume, core temperature, subcutaneous temperature, or muscular activity of the patient. In such embodiments, processor 46 may periodically determine the heart rate, measured value of one or more ECG morphological features, respiration rate, respiratory volume, core temperature, subcutaneous temperature, or muscular activity level of a patient 12 based on the signal. The determined values of these parameters may be mean or median values.

Sensors 40 may include electrodes located on leads 16 or integrated as part of the housing of IMDs 14 that generates an electrogram signal as a function of electrical activity of the heart of a patient 12, and processor 46 may periodically determine the heart rate of a patient 12 based on the electrogram signal. In other embodiments, a sensor 40 may include an acoustic sensor within IMDs 14, a pressure sensor within the bloodstream or cerebrospinal fluid of a patient 12, or a temperature sensor located within the bloodstream of the patient 12. The signals generated by such sensors 40 may vary as a function of contraction of the heart of a patient 12, and can be used by processor 46 to periodically determine the heart rate of the patient 12.

In some embodiments, processor 46 may detect, and measure values for one or more ECG morphological features within an electrogram generated by electrodes as described above. ECG morphological features may vary in a manner that indicates the activity level of patient. For example, the amplitude of the ST segment of the ECG may increase with increased patient activity. Further, the amplitude of QRS complex or T-wave may increase, and the widths of the QRS complex and T-wave may decrease with increased patient activity. The QT interval and the latency of an evoked response may decrease with increased patient activity, and the amplitude of the evoked response may increase with increased patient activity.

Sensors 40 may include an electrode pair, including one electrode integrated with the housing of IMDs 14 and one of electrodes 42, as described above. In some embodiments, such an electrode pair may generate a signal as a function of the thoracic impedance of a patient 12, which varies as a function of respiration by the patient 12. In other embodiments, sensors 40 may include a strain gauge, bonded piezoelectric element, or pressure sensor within the blood or cerebrospinal fluid that generates a signal that varies based on patient respiration. Processor 46 may monitor the signals generated by such sensors 40 to periodically determine a respiration rate and/or respiratory volume of a patient 12. An electrogram generated by electrodes as discussed above may also be modulated by patient respiration, and processor 46 may use the electrogram as an indirect representation of respiration rate.

In some embodiments, sensors 40 may include one or more electrodes that generate an electromyogram (EMG) signal as a function of muscle electrical activity. The amplitude and/or frequency of an EMG signal may vary based on the activity level of a patient. The electrodes may be, for example, located in the legs, abdomen, chest, back or buttocks of a patient 12 to detect muscle activity associated with walking, running, or the like. The electrodes may be coupled to IMDs 14 wirelessly or by leads 16 or, if IMDs 14 are implanted in these locations, integrated with a housing of a respective one of IMDs 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to IMDs 14 wirelessly or via respective leads 16, or piezoelectric crystals may be bonded to the can of IMDs 14 when the IMD is implanted in these areas, e.g., in the back, chest buttocks or abdomen of a patient 12.

In alternative embodiments, sensors 40 may be configured for placement within or around the brain of a patient 12 to detect the onset, magnitude, or duration of a neurological disorder. For example, sensors 40 may detect the onset of an epileptic seizure and track the duration and extent of the seizure. IMDs 14 may compare neurological events to physical activity to determine how the neurological events affect physical activity. IMDs 14 may also initiate or change electrical stimulation when a neurological event is detected.

Further, sensors 40 may include any of a variety of known temperature sensors to generate a signal as a function of a core or subcutaneous temperature of a patient 12. Core or subcutaneous temperature may vary as a function of the activity level of a patient 12. Such temperature sensors may be incorporated within the housing of IMDs 14, or coupled to IMDs 14 wirelessly or via leads.

In some embodiments, processor 46 compares a determined value of such a physiological parameter to one or more thresholds or a look-up table stored in memory to determine a number of activity counts, and stores the determined number of activity counts in memory 48 as a determined activity level. In other embodiments, processor 46 may store the determined physiological parameter value as a determined activity level. The use of activity counts, however, may allow processor 46 to determine an activity level based on a plurality of signals generated by a plurality of sensors 40. For example, processor 46 may determine a first number of activity counts based on a sample of an accelerometer signal and a second number of activity counts based on a heart rate determined from an electrogram signal at the time the accelerometer signal was sampled. Processor 46 may determine an activity level by calculating the sum or average, which may be a weighted sum or average, of first and second activity counts.

Processor 46 may record activity levels continuously or periodically, e.g., one sample every minute or continuously for ten minutes each hour. In some embodiments, processor 46 limits recording of activity levels to relevant time periods, i.e., when a patient 12 is awake or likely to be awake, and therefore likely to be active. For example, patient may indicate via patient programmer 26 when patient is attempting to sleep or awake. Processor 46 may receive these indications via a telemetry circuit 50 of IMDs 14, and may suspend or resume recording of activity levels based on the indications. In other embodiments, processor 46 may maintain a real-time clock, and may record activity levels based on the time of day indicated by the clock, e.g., processor 46 may limit activity level recording to daytime hours.

Further, processor 46 may determine when a patient is asleep, attempting to sleep, or awake by monitoring one or more physiological parameters of the patient based on the signals generated by sensors 40. Processor 46 may for example, limit activity monitoring to times when the patient is not asleep or attempting to sleep. For example, processor 46 may determine when patient 12 is attempting to sleep by monitoring the posture of patient 12 to determine when patient 12 is recumbent using any of the posture monitoring sensors 40 or techniques described above. As an example, sensors 40 may include a plurality of orthogonally arranged accelerometers, as discussed above, and processor 46 may monitor the DC components of the signals generated by the accelerometers to determine when patient is recumbent.

In other embodiments, processor 46 determines when a patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluid, and estimate the time that the patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that patient 12 is attempting to fall asleep as the time that the threshold is exceeded, or some amount of time after the threshold is exceeded. Any of a variety of combinations or variations of the above-described techniques may be used to determine when a patient 12 is attempting to fall asleep, and a specific one or more techniques may be selected based on the sleeping and activity habits of a particular patient.

In order to determine whether a patient 12 is asleep, processor 46 may monitor any one or more physiological parameters that discernibly change when the patient 12 falls asleep, such as activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response. Processor 46 may additionally or alternatively monitor the variability of one or more of these physiological parameters, such as heart rate and respiration rate, which may discernible change when a patient 12 is asleep. Further details regarding monitoring physiological parameters to identify when a patient is attempting to sleep and when the patient is asleep may be found in a commonly-assigned and co-pending U.S. Pat. No. 8,055,348 by Kenneth Heruth et al., entitled "DETECTING SLEEP TO EVALUATE THERAPY," which was filed on Mar. 26, 2007 and issued on Nov. 8, 2011, and is incorporated herein by reference in its entirety.

For example, in some embodiments, processor 46 may determine whether a patient 12 is asleep by analyzing an electroencephalogram (EEG) signal from the patient. EEG analysis is not limited to embodiments which include leads 16 implanted on or within brain 19 of patient. Nonetheless, system 10B, illustrated in FIGS. 1B and 2B, is an example of a system that includes electrodes 42, located on or within the brain of patient 12B, that are coupled to IMD 14B. As shown in FIG. 2B, electrodes 42 may be selectively coupled to therapy module 44 or an EEG signal module 54 by a multiplexer 52, which operates under the control of processor 46. EEG signal module 54 receives signals from a selected set of the electrodes 42 via multiplexer 52 as controlled by processor 46. EEG signal module 54 may analyze the EEG signal for certain features indicative of sleep or different sleep states, and provide indications of relating to sleep or sleep states to processor 46. Thus, electrodes 42 and EEG signal module 54 may be considered another sensor 40 in system 10B. IMD 14B may include circuitry (not shown) that conditions the EEG signal such that it may be analyzed by processor 52. For example, IMD 14B may include one or more analog to digital converters to convert analog signals received from electrodes 42 into digital signals usable by processor 46, as well as suitable filter and amplifier circuitry.

Processor 46 may direct EEG signal module to analyze the EEG signal to determine whether patient 12B is sleeping, and such analysis may be considered alone or in combination with other physiological parameters to determine whether patient 12B is asleep. EEG signal module 60 may process the EEG signals to detect when patient 12 is asleep using any of a variety of techniques, such as techniques that identify whether a patient is asleep based on the amplitude and/or frequency of the EEG signals. In some embodiments, the functionality of EEG signal module 54 may be provided by processor 46, which, as described above, may include one or more microprocessors, ASICs, or the like.

In other embodiments, processor 46 may record activity levels in response to receiving an indication from a patient 12 via patient programmer 26. For example, processor 46 may record activity levels during times when a patient 12 believes the therapy delivered by IMDs 14 is ineffective and/or the symptoms experienced by a patient 12 have worsened. In this manner, processor 46 may limit data collection to periods in which more probative data is likely to be collected, and thereby conserve a battery and/or storage space within memory 48.

Further, as described above, the invention is not limited to embodiments in which IMDs 14 determines activity levels. In some embodiments, processor 46 may periodically store samples of the signals generated by sensors 40 in memory 48, rather than activity levels, and may associate those samples with the current therapy parameter set.

Figure 3:
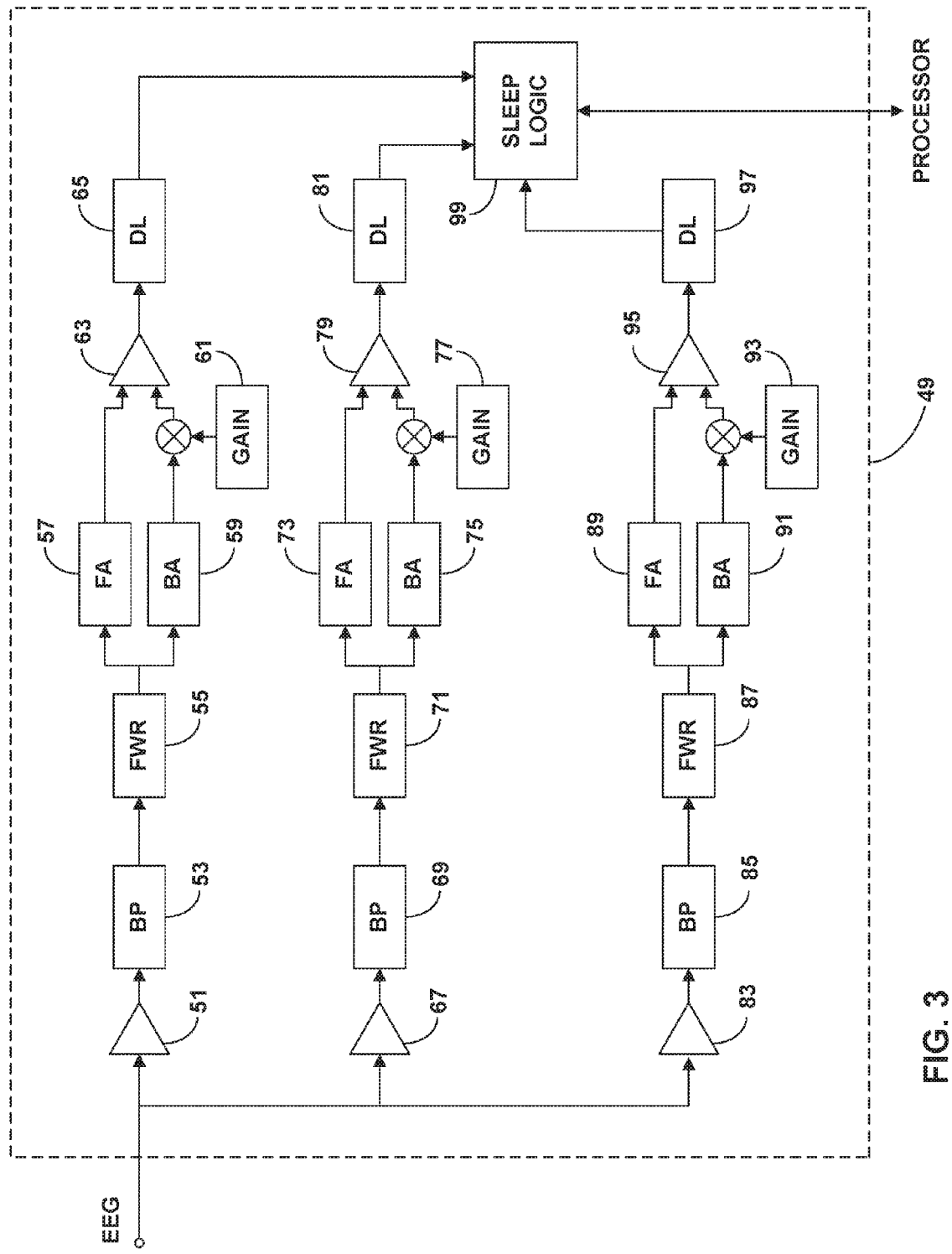
FIG. 3 is a logic diagram illustrating an example circuit that detects the sleep state of a patient from the electroencephalogram (EEG) signal.

FIG. 3 is a logical diagram of an example circuit that detects sleep and/or sleep type of a patient based on the electroencephalogram (EEG) signal. The circuit may additionally or alternatively detect an awake state when the patient is not in any sleep state. As shown in FIG. 3, module 49 may be integrated into an EEG signal module of an IMD 14 or a separate implantable or external device capable of detecting an EEG signal. An EEG signal detected by electrodes adjacent to the brain of patient 12 is transmitted into module 49 and provided to three channels, each of which includes a respective one of amplifiers 51, 67 and 83, and bandpass filters 53, 69 and 85. In other embodiments, a common amplifier amplifies the EEG signal prior to filters 53, 69 and 85.

Bandpass filter 53 allows frequencies between approximately 4 Hz and approximately 8 Hz, and signals within the frequency range may be prevalent in the EEG during S1 and S2 sleep states. Bandpass filter 69 allows frequencies between approximately 1 Hz and approximately 3 Hz, which may be prevalent in the EEG during the S3 and S4 sleep states. Bandpass filter 85 allows frequencies between approximately 10 Hz and approximately 50 Hz, which may be prevalent in the EEG during REM sleep. Each resulting signal may then be processed to identify in which sleep state a patient 12 is.

After bandpass filtering of the original EEG signal, the filtered signals are similarly processed in parallel before being delivered to sleep logic module 99. For ease of discussion, only one of the three channels will be discussed herein, but each of the filtered signals would be processed similarly.

Once the EEG signal is filtered by bandpass filter 53, the signal is rectified by full-wave rectifier 55. Modules 57 and 59 respectively determine the foreground average and background average so that the current energy level can be compared to a background level at comparator 63. The signal from background average is increased by gain 61 before being sent to comparator 63, because comparator 63 operates in the range of millivolts or volts while the EEG signal amplitude is originally on the order of microvolts. The signal from comparator 63 is indicative of sleep stages S1 and S2. If duration logic 65 determines that the signal is greater than a predetermined level for a predetermined amount of time, the signal is sent to sleep logic module 99 indicating that a patient 12 may be within the S1 or S2 sleep states. In some embodiments, as least duration logic 65, 81, 97 and sleep logic 99 may be embodied in a processor of the device containing EEG module 49.

Module 49 may detect all sleep types for a patient 12. Further, the beginning of sleep may be detected by module 49 based on the sleep state of a patient 12. Some of the components of module 49 may vary from the example of FIG. 3. For example, gains 61, 77 and 93 may be provided from the same power source. Module 49 may be embodied as analog circuitry, digital circuitry, or a combination thereof.

In other embodiments, FIG. 3 may not need to reference the background average to determine the current state of sleep of a patient 12. Instead, the power of the signals from bandpass filters 53, 69 and 85 are compared to each other, and sleep logic module 99 determines which the sleep state of a patient 12 based upon the frequency band that has the highest power. In this case, the signals from full-wave rectifiers 55, 71 and 87 are sent directly to a device that calculates the signal power, such as a spectral power distribution module (SPD), and then to sleep logic module 99 which determines the frequency band of the greatest power, e.g., the sleep state of a patient 12. In some cases, the signal from full-wave rectifiers 55, 71 and 87 may be normalized by a gain component to correctly weight each frequency band.

Figure 4:
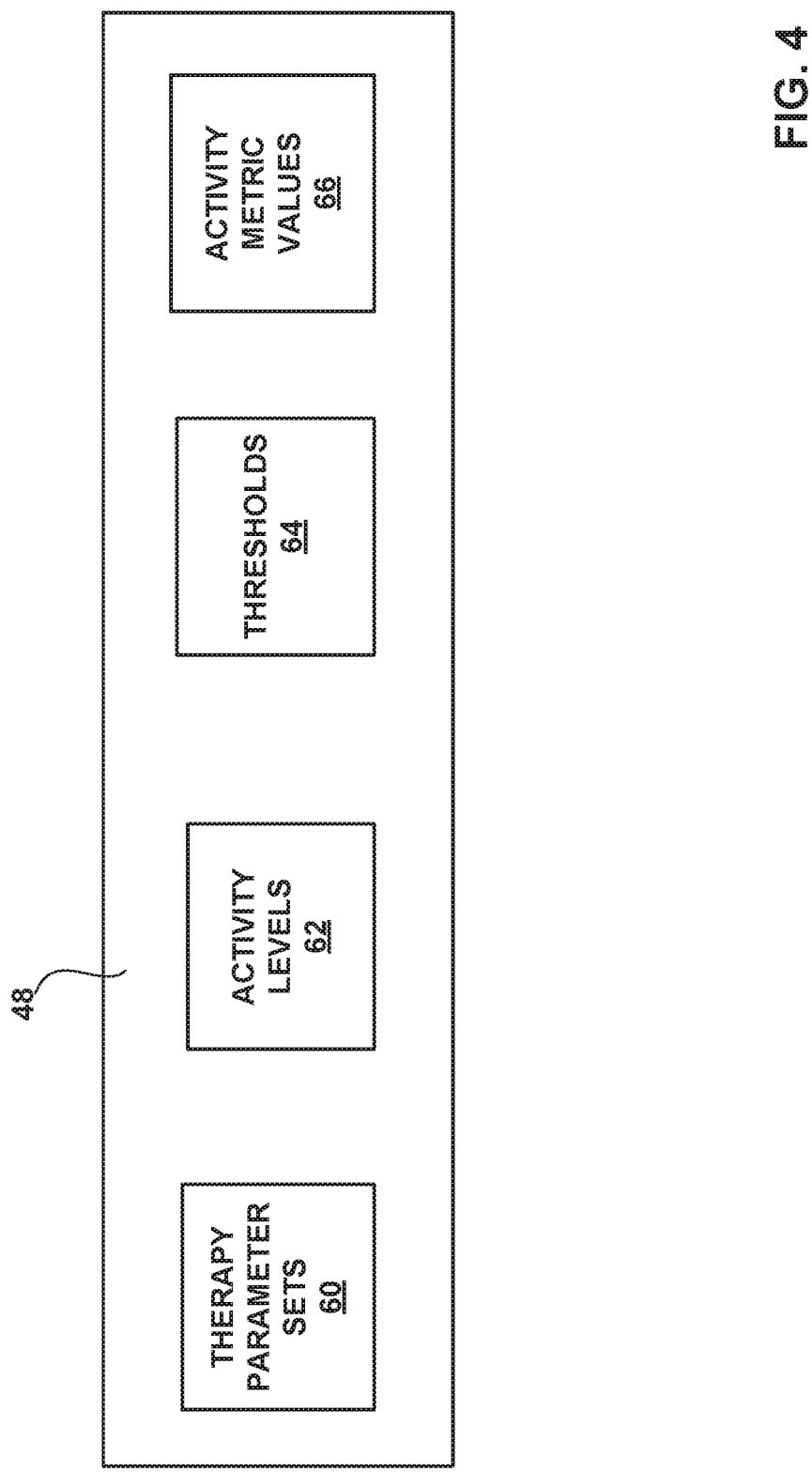
FIG. 4 is a block diagram illustrating an example memory of the implantable medical devices of FIGS. 1A and 1B.

FIG. 4 illustrates memory 48 of an IMD 14 in greater detail. As shown in FIG. 4, memory 48 stores information describing a plurality of therapy parameter sets 60. Therapy parameter sets 60 may include parameter sets specified by a clinician using clinician programmer 20. Therapy parameter sets 60 may also include parameter sets that are the result of a patient 12 changing one or more parameters of one of the preprogrammed therapy parameter sets. For example, a patient 12 may change parameters such as pulse amplitude, frequency or pulse width via patient programmer 26.

Memory 48 also stores the activity levels 62 determined by processor 46. When processor 46 determines an activity level as discussed above, processor 46 associates the determined activity level with the current one of therapy parameter sets 60, e.g., the one of therapy parameter sets 60 that processor 46 is currently using to control delivery of therapy by therapy module 44 to a patient 12. For example, processor 46 may store determined activity levels 62 within memory 48 with an indication of the parameter sets 60 with which they are associated. In other embodiments, processor 46 stores samples (not shown) of signals generated by sensors 40 within memory 48 with an indication of the parameter sets 60 with which they are associated.

In some embodiments, processor 46 determines a value of one or more activity metrics for each of therapy parameter sets 60 based on the activity levels 62 associated with the parameter sets 60. Processor 46 may store the determined activity metric values 66 within memory 48 with an indication as to which of therapy parameter sets 60 the determined values are associated with. For example, processor 46 may determine a mean or median of activity levels associated with a therapy parameter set, and store the mean or median activity level as an activity metric value 66 for the therapy parameter set.

In embodiments in which activity levels 62 comprise activity counts, processor 46 may store, for example, an average number of activity counts per unit time as an activity metric value. An average number of activity counts over a period substantially between ten and sixty minutes, for example, may provide a more accurate indication of activity than an average over shorter periods by ameliorating the effect of transient activities on an activity signal or physiological parameters. For example, rolling over in bed may briefly increase the amplitude of an activity signal and a heart rate, thereby confounding the activity analysis.

In other embodiments, processor 46 may compare a mean or median activity level to one or more threshold values 64, and may select an activity metric value from a predetermined scale of activity metric values based on the comparison. The scale may be numeric, such as activity metric values from 1-10, or qualitative, such as low, medium or high activity. The scale of activity metric values may be, for example, stored as a look-up table within memory 48. Processor 46 stores the activity metric value 66 selected from the scale within memory 48.

In some embodiments, processor 46 compares each activity level 62 associated with a therapy parameter set 60 to one or more threshold values 64. Based on the comparison, processor 46 may determine percentages of time above and/or below the thresholds, or within threshold ranges. Processor 46 may store the one or more determined percentages within memory 48 as one or more activity metric values 66 for that therapy parameter set. In other embodiments, processor 46 compares each activity level 62 associated with a therapy parameter set 66 to a threshold values 64, and determines an average length of time that consecutively recorded activity levels 62 remained above the threshold as an activity metric value 66 for that therapy parameter set.

In some embodiments, processor 46 determines a plurality of activity metric values for each of the plurality of therapy parameter sets, and determines an overall activity metric value for a parameter set based on the values of the individual activity metrics for that parameter set. For example, processor 46 may use the plurality of individual activity metric values as indices to identify an overall activity metric value from a look-up table stored in memory 48. Processor 46 may select the overall metric value from a predetermined scale of activity metric values, which may be numeric, such as activity metric values from 1-10, or qualitative, such as low, medium or high activity.

As shown in FIGS. 2A and 2B, IMDs 14 include a telemetry circuit 50, and processor 46 communicates with programmers 20, 26 via telemetry circuit 50. In some embodiments, processor 46 provides information identifying therapy parameter sets 60 and activity metric values 66 associated with the parameter sets to programmer 20, and programmer 20 displays a list of therapy parameter sets 60 and associated activity metric values 66. In other embodiments, as will be described in greater detail below, processor 46 does not determine activity metric values 66. Instead, processor 46 provides activity levels 62 to programmer 20 via telemetry circuit 50, and programmer 20 determines activity metric values 66 for display to the clinician. Further, in other embodiments, processor 46 provides samples of signals generated by sensors 40 to programmer 20 via telemetry circuit 50, and programmer 20 may determine both activity levels 62 and activity metric values 66 based on the samples. Some external medical device embodiments of the invention include a display, and a processor of such an external medical device may both determine activity metric values 66 and display a list of therapy parameter sets 60 and associated activity metric values 66 to a clinician.

Figure 5:
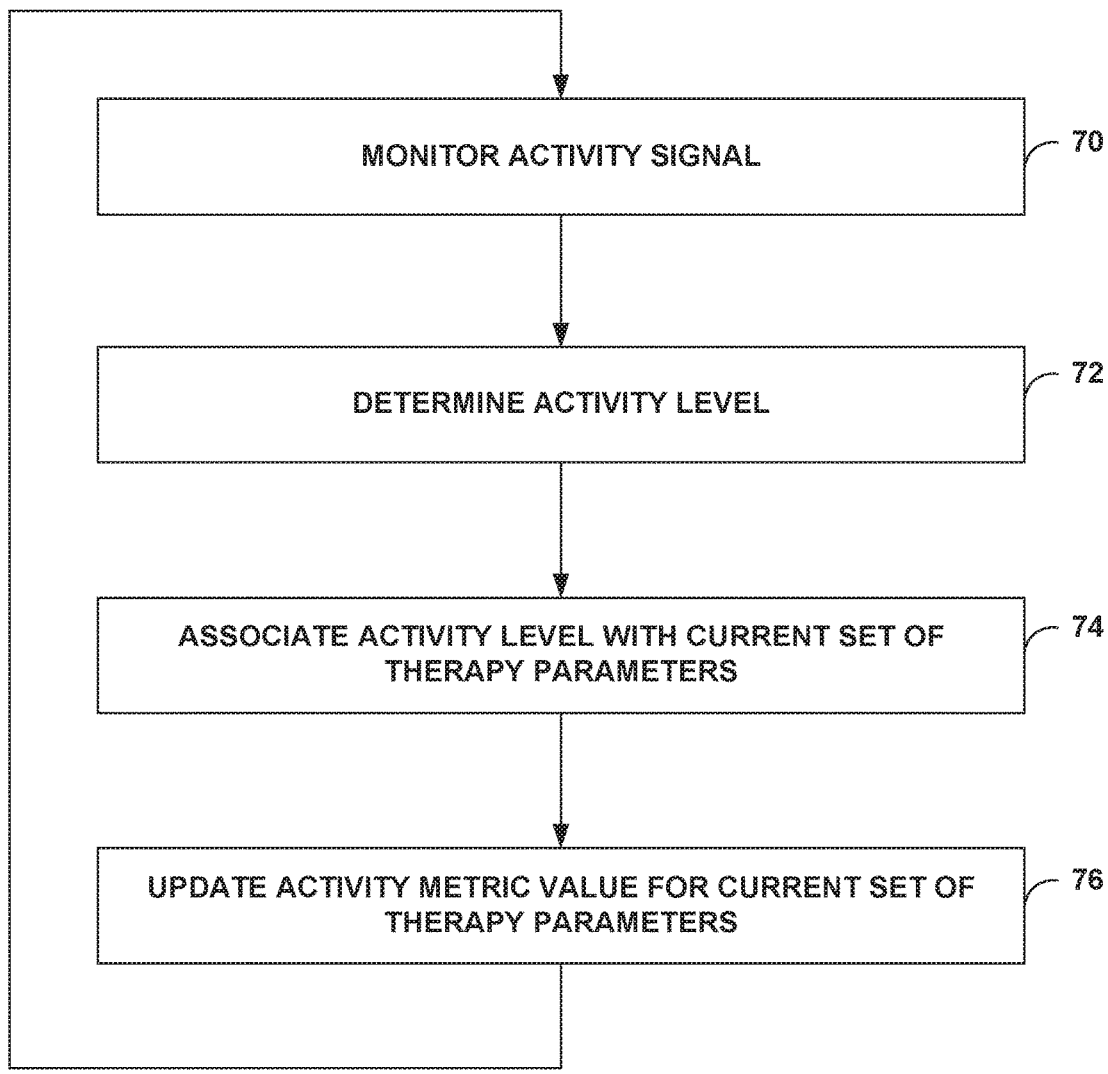
FIG. 5 is a flow diagram illustrating an example method for collecting activity information that may be employed by an implantable medical device.

FIG. 5 is a flow diagram illustrating an example method for collecting activity information that may be employed by an IMD 14. An IMD 14 monitors one or more activity signals (70). For example, an IMD 14 may monitor a signal generated by an accelerometer or piezoelectric crystal, and/or a signal that indicates a physiological parameter that varies as a function of patient activity, such heart rate, ECG morphology, respiration rate, respiratory volume, core temperature, subcutaneous temperature, or muscle activity.

An IMD 14 determines an activity level 62 (72). For example, an IMD 14 may determine a number of activity counts based on the one or more signals, as described above. An IMD 14 identifies the current therapy parameter set 60, and associates the determined activity level 62 with the current therapy parameter set 60 (74). For example, an IMD 14 may store the determined activity level 62 in memory 48 with an indication of the current therapy parameter set 60.

An IMD 14 may then update one or more activity metric values 66 associated with the current therapy parameter set 60, as described above (76).

An IMD 14 may periodically perform the example method illustrated in FIG. 5, e.g., may periodically monitor the activity signal (70), determine activity levels 62 (72), and associate the determined activity levels 62 with a current therapy parameter set 60 (74). As described above, an IMD 14 may only perform the example method during daytime hours, or when a patient is awake and not attempting to sleep, and/or only in response to an indication received from a patient 12 via patient programmer 20. An IMD 14 need not update activity metric values 66 each time an activity level 62 is determined. In some embodiments, for example, an IMD 14 may store activity levels 62 within memory, and may determine the activity metric values 66 upon receiving a request for the values from clinician programmer 20. In alternative examples, an IMD 14 may associate activity levels 62 and/or detection of neurological events with a current therapy parameter set 60. In addition, a patient 12 may manually input the occurrence of a neurological event for use by an IMD 14.

Further, in some embodiments, as will be described in greater detail below, an IMD 14 does not determine the activity metric values 66, but instead provides activity levels 62 to a computing device, such as clinician programmer 20 or patient programmer 26. In such embodiments, the computing device determines the activity metric values 66 associated with each of the therapy parameter sets 60. Additionally, as described above, IMD 14 need not determine activity levels 62, but may instead store samples of the signals generated by sensors 40. In such embodiments, the computing device may determine both activity levels 62 and activity metric values 66 based on the samples.

Figure 6:
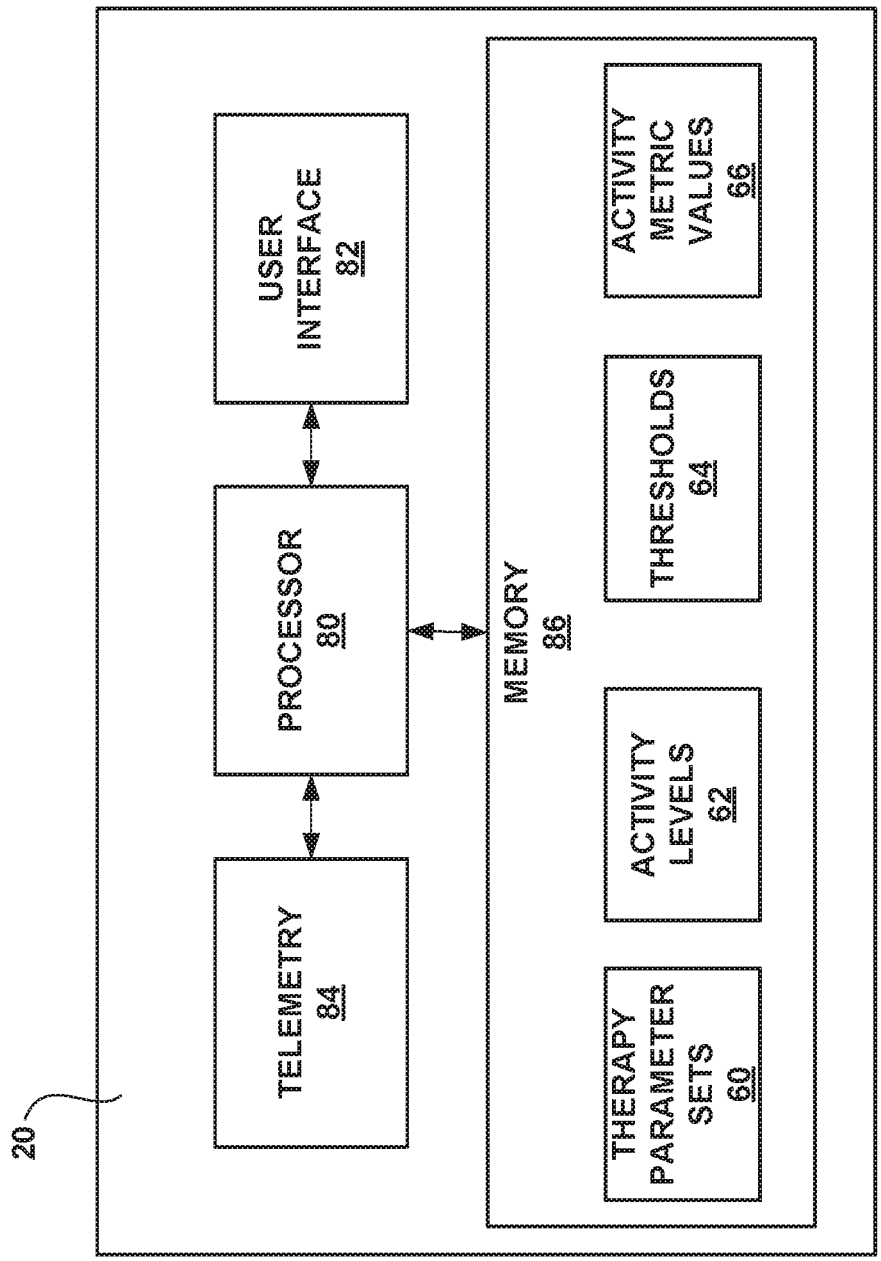
FIG. 6 is a block diagram illustrating an example clinician programmer.

FIG. 6 is a block diagram illustrating clinician programmer 20. A clinician may interact with a processor 80 via a user interface 82 in order to program therapy for a patient 12, e.g., specify therapy parameter sets. Processor 80 may provide the specified therapy parameter sets to an IMD 14 via telemetry circuit 84.

At another time, e.g., during a follow up visit, processor 80 may receive information identifying a plurality of therapy parameter sets 60 from an IMD 14 via telemetry circuit 84, which may be stored in a memory 86. The therapy parameter sets 60 may include the originally specified parameter sets, and parameter sets resulting from manipulation of one or more therapy parameters by a patient 12 using patient programmer 26. In some embodiments, processor 80 also receives activity metric values 66 associated with the therapy parameter sets 60, and stores the activity metric values in memory 86.

In other embodiments, processor 80 receives activity levels 62 associated with the therapy parameter sets 60, and determines values 66 of one or more activity metrics for each of the plurality of therapy parameter sets 60 using any of the techniques described above with reference to an IMD 14 and FIGS. 2A, 2B and 4. Processor 80 may, for example, use threshold values 64 stored in memory 86 to determine activity metric values 66, as described above. In still other embodiments, processor 80 receives samples of activity signals from IMD 14, and determines activity levels 62 and activity metric values 66 based on signals using any of the techniques described above with reference to an IMD 14 and FIGS. 2 and 3.

Upon receiving or determining activity metric values 66, processor 80 generates a list of the therapy parameter sets 60 and associated activity metric values 66, and presents the list to the clinician. User interface 82 may include display 22, and processor 80 may display the list via display 22. The list of therapy parameter sets 60 may be ordered according to the associated activity metric values 66. Where a plurality of activity metric values are associated with each of the parameter sets, the list may be ordered according to the values of the activity metric selected by the clinician. Processor 80 may also present other activity information to a user, such as a trend diagram of activity over time, or a histogram, pie chart, or other illustration of percentages of time that activity levels 62 were within certain ranges. Processor 80 may generate such charts or diagrams using activity levels 62 associated with a particular one of the therapy parameter sets 66, or all of the activity levels 62 recorded by IMD 14.

User interface 82 may include display 22 and keypad 24, and may also include a touch screen or peripheral pointing devices as described above. Processor 80 may include a microprocessor, a controller, a DSP, an ASIC, an FPGA, discrete logic circuitry, or the like. Memory 86 may include program instructions that, when executed by processor 80, cause clinician programmer 20 to perform the functions ascribed to clinician programmer 20 herein. Memory 86 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

In some embodiments, clinician programmer 20 may be a patient programmer that is used by a patient 12 to input physical activity, modify physical activity stored by an IMD 14, or input neurological events or occurrences. The input from a patient 12 may be used by an IMD 14 to track physical activity of a patient 12, neurological events, or any other physiological event of the patient. An IMD 14 or programmer 20 may associate events to stimulation parameters used during those events. In addition, the input from a patient 12 may be used to initiate, stop, or adjust electrical stimulation in order to facilitate efficacious stimulation therapy.

FIG. 7 illustrates an example list 90 of therapy parameter sets and associated activity metric values 66 that may be presented by clinician programmer 20. Each row of example list 90 includes an identification of one of therapy parameter sets 60, the parameters of the therapy parameter set, and values 66 associated with the therapy parameter set for each of two illustrated activity metrics. Programmer 20 may order list 90 according to a user-selected one of the activity metrics.

Figure 10:
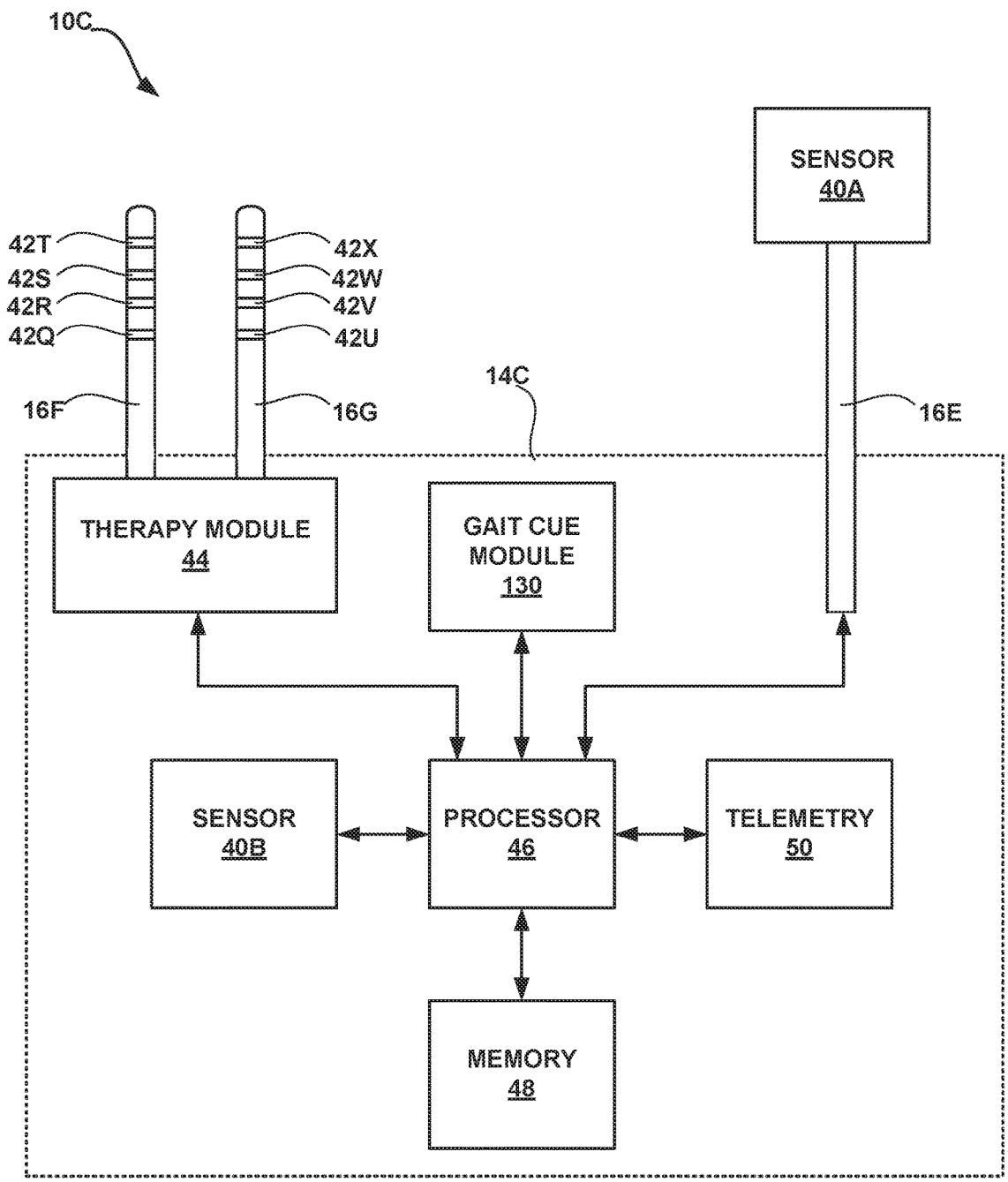
FIG. 10 is a block diagram illustrating an example system including implantable medical device that collects activity information, and further identifies and responds to gait freeze events.

The activity metrics illustrated in FIG. 7 are a percentage of time active, and an average number of activity counts per hour. An IMD 14 or programmer 20 may determine the average number of activity counts per hour for one of the illustrated therapy parameter sets by identifying the total number of activity counts associated with the parameter set and the total amount of time that IMD 14 was using the parameter set. An IMD 14 or programmer 20 may determine the percentage of time active for one of parameter sets 60 by comparing each activity level 62 associated with the parameter set to an "active" threshold, and determining the percentage of activity levels 62 above the threshold. As illustrated in FIG. 10, an IMD 14 or programmer 20 may also compare each activity level for the therapy parameter set to an additional, "high activity" threshold, and determine a percentage of activity levels 62 above that threshold.

Figure 8:
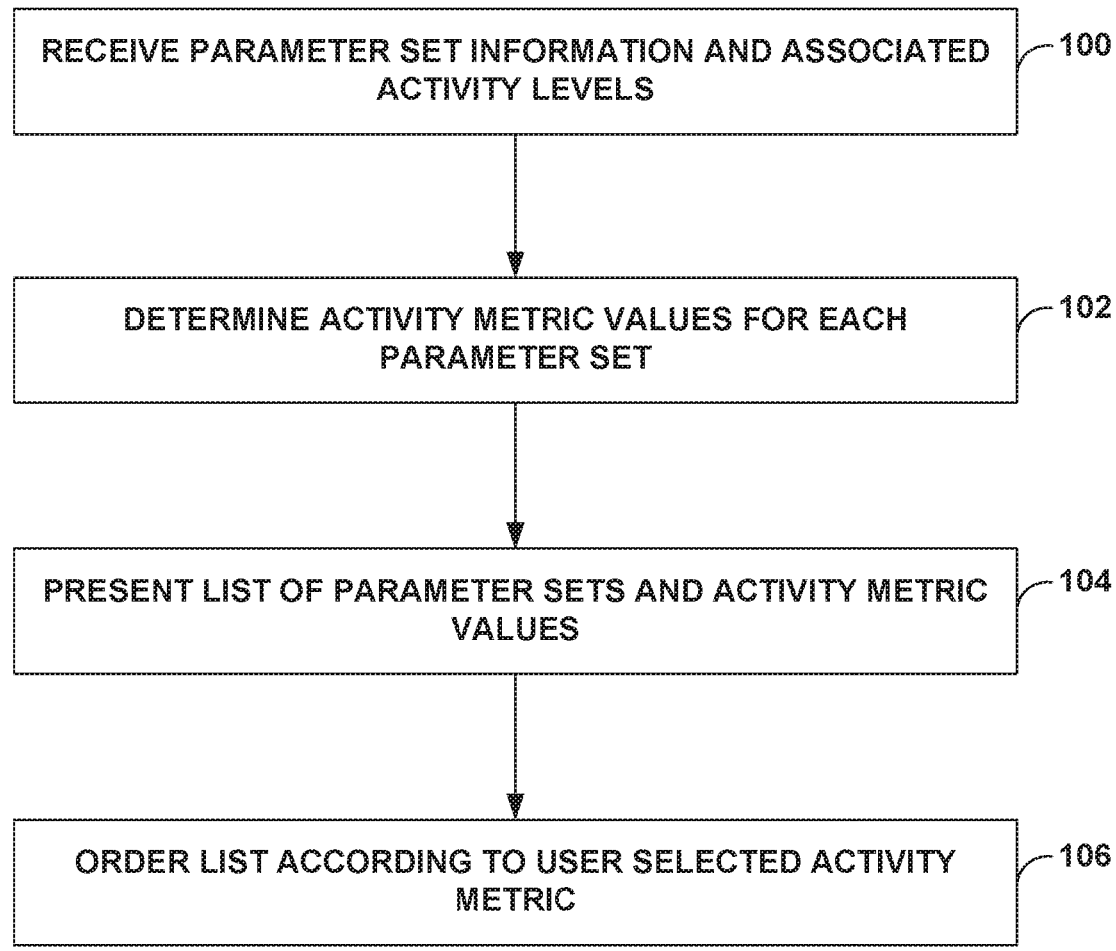
FIG. 8 is a flow diagram illustrating an example method for displaying a list of therapy parameter sets and associated activity metric values that may be employed by a clinician programmer.

FIG. 8 is a flow diagram illustrating an example method for displaying a list of therapy parameter sets 60 and associated activity metric values 66 that may be employed by a clinician programmer 20. Programmer 20 receives information identifying therapy parameter sets 60 and associated activity levels 62 from an IMD 14 (100). In addition, programmer 20 may receive neurological events from an IMD 14. Programmer 20 then determines one or more activity metric values 66 for each of the therapy parameter sets based on the activity levels 62, and/or neurological events, associated with the therapy parameter sets (102). In other embodiments, an IMD 14 determines the activity metric values 66, and provides them to programmer 20, or provides samples of activity signals associated with therapy parameter sets to programmer 20 for determination of activity metric values, as described above. After receiving or determining activity metric values 66, programmer 20 presents a list 90 of therapy parameter sets 60 and associated activity metric values 66 to the clinician, e.g., via display 22 (104). Programmer 20 may order list 90 of therapy parameter sets 60 according to the associated activity metric values 66, and the clinician may select which of a plurality of activity metrics list 90 is ordered according to via a user interface 82 (106).

The invention is not limited to embodiments in which a programming device receives information from the medical device, or presents information to a user. Other computing devices, such as handheld computers, desktop computers, workstations, or servers may receive information from the medical device and present information to a user as described herein with reference to programmers 20, 26. A computing device, such as a server, may receive information from the medical device and present information to a user via a network, such as a local area network (LAN), wide area network (WAN), or the Internet. Further, in some embodiments, the medical device is an external medical device, and may itself include user interface and display to present activity or gait information to a user, such as a clinician or patient, for evaluation of therapy parameter sets.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Activity metric values collected during use of the trial neurostimulator or pump, which may be related to overall activity and gait, may be used by a clinician to evaluate the prospective therapy parameter sets, and select parameter sets for use by the later implanted non-trial neurostimulator or pump. For example, a trial neurostimulator or pump may determine values of one or more activity metrics for each of a plurality of prospective therapy parameter sets, and a clinician programmer may present a list of prospective parameter sets and associated activity metric values to a clinician. The clinician may use the list to identify potentially efficacious parameter sets, and may program a permanent implantable neurostimulator or pump for the patient with the identified parameter sets.

Additionally, the invention is not limited to embodiments in which the therapy delivering medical device monitors the physiological parameters of the patient described herein. In some embodiments, a separate monitoring device monitors values of one or more physiological parameters of the patient instead of, or in addition to, a therapy delivering medical device. The monitor may include a processor 46 and memory 48, and may be coupled to or include sensors 40, as illustrated above with reference to an IMD 14 and FIGS. 2A, 2B and 3. The monitor may determine activity metric values based on the values of the monitored physiological parameter values, or may transmit activity levels, gait parameters, or the physiological parameter values or signals to a computing device for determination of the activity metric values.

In embodiments in which the medical device determines activity metric values, the medical device may identify the current therapy parameter set when a value of one or more activity metric values metrics is collected, and may associate that value with the therapy parameter set. In embodiments in which a programming device or other computing device determines activity levels, gait parameters, gait freeze events, or activity metric values, the medical device may associate recorded physiological parameter values or signals with the current therapy parameter set in the memory. Further, in embodiments in which a separate monitoring device records physiological parameter values or signals, or determines activity levels, gait parameters, gait freeze event, or activity metric values, the monitoring device may mark recorded physiological parameter values, activity levels, or activity metric values with a current time in a memory, and the medical device may store an indication of a current therapy parameter set and time in a memory. A programming device of other computing device may receive indications of the physiological parameter values, activity levels, gait parameters, gait freeze events, or activity metric values and associated times from the monitoring device, as well as indications of the therapy parameter sets and associated times from the medical device, and may associate the physiological parameter values, activity levels, gait parameters, gait freeze events, or activity metric values with the therapy parameter set that was delivered by the medical device when the values, parameters, events or levels were recorded.

Figure 9:
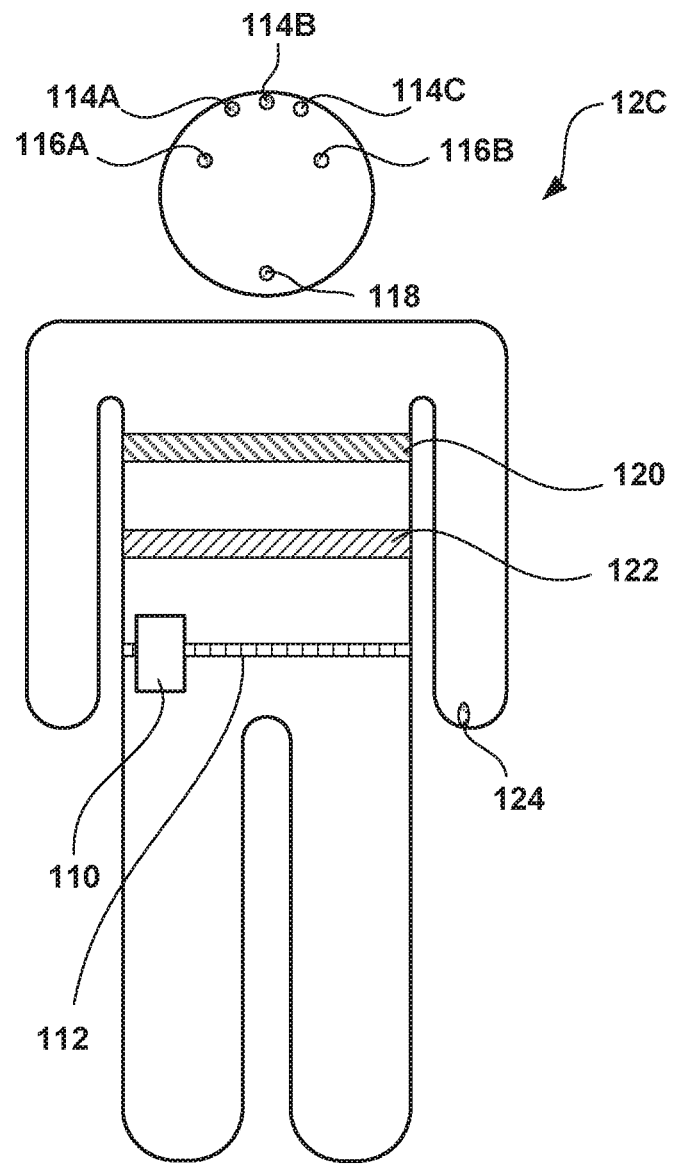
FIG. 9 is a conceptual diagram illustrating a monitor that monitors values of one or more physiological parameters of the patient.

FIG. 9 is a conceptual diagram illustrating a monitor 110 that monitors values of one or more physiological parameters of the patient instead of, or in addition to, a therapy delivering medical device as described above. Monitor 110 may determine activity metric values, or provide physiological parameter values, activity levels, gait parameters, or gait freeze event information to another device, as described above.

In the illustrated example, monitor 110 is configured to be attached to or otherwise carried by a belt 112, and may thereby be worn by patient 12C. FIG. 9 also illustrates various sensors 40 that may be coupled to monitor 110 by leads, wires, cables, or wireless connections, such as EEG electrodes 114A-C placed on the scalp of patient 12C, a plurality of EOG electrodes 116A and 116B placed proximate to the eyes of patient 12C, and one or more EMG electrodes 118 placed on the chin or jaw the patient. The number and positions of electrodes 114, 116 and 118 illustrated in FIG. 9 are merely exemplary. For example, although only three EEG electrodes 174 are illustrated in FIG. 1, an array of between 16 and 25 EEG electrodes 114 may be placed on the scalp of patient 12C, as is known in the art. EEG electrodes 114 may be individually placed on patient 12C, or integrated within a cap or hair net worn by the patient. Signals received from EEG electrodes 114A-C may be analyzed to determine whether patient 12C is asleep, e.g., using techniques and circuitry described with reference to FIG. 3.

In the illustrated example, patient 12C wears an ECG belt 120. ECG belt 120 incorporates a plurality of electrodes for sensing the electrical activity of the heart of patient 12C. The heart rate and, in some embodiments, ECG morphology of patient 12C may monitored by monitor 110 based on the signal provided by ECG belt 120. Examples of suitable belts 120 for sensing the heart rate of patient 12C are the "M" and "F" heart rate monitor models commercially available from Polar Electro. In some embodiments, instead of belt 120, patient 12C may wear a plurality of ECG electrodes attached, e.g., via adhesive patches, at various locations on the chest of the patient, as is known in the art. An ECG signal derived from the signals sensed by such an array of electrodes may enable both heart rate and ECG morphology monitoring, as is known in the art.

As shown in FIG. 9, patient 12C may also wear a respiration belt 122 that outputs a signal that varies as a function of respiration of the patient. Respiration belt 122 may be a plethysmograpy belt, and the signal output by respiration belt 122 may vary as a function of the changes is the thoracic or abdominal circumference of patient 12C that accompany breathing by the patient. An example of a suitable belt 122 is the TSD201 Respiratory Effort Transducer commercially available from Biopac Systems, Inc. Alternatively, respiration belt 122 may incorporate or be replaced by a plurality of electrodes that direct an electrical signal through the thorax of the patient, and circuitry to sense the impedance of the thorax, which varies as a function of respiration of the patient, based on the signal. In some embodiments, ECG and respiration belts 120 and 122 may be a common belt worn by patient 12C, and the relative locations of belts 120 and 122 depicted in FIG. 9 are merely exemplary.

In the example illustrated by FIG. 9, patient 12C also wears a transducer 124 that outputs a signal as a function of the oxygen saturation of the blood of patient 12C. Transducer 124 may be an infrared transducer. Transducer 124 may be located on one of the fingers or earlobes of patient 12C. Sensors 40 coupled to monitor 110 may additionally or alternatively include or be coupled to any of the variety of sensors 40 described above with reference to FIG. 2 that output signals that vary as a function of patient activity, such as EMG electrodes, accelerometers, piezoelectric crystals, or pressure sensors.

As discussed above, the overall activity level of a patient, e.g., the extent to which the patient is on his or her feet and moving or otherwise active, rather than sitting or lying in place, may be negatively impacted by any of a variety of ailments or symptoms.

Accordingly, the activity level of a patient may reflect the efficacy of a particular therapy or therapy parameter set in treating the ailment or symptom. In other words, it may generally be the case that the more efficacious a therapy parameter set is, the more active the patient will be. In addition, the activity level of a patient may reflect the efficacy of particular therapy parameters. The activity level may be correlated with neurological events as an indication of therapy efficacy in treating neurological disorders as described above.

As discussed above, in accordance with the invention, activity levels may be monitored during delivery of therapy according to a plurality of therapy parameter sets, and used to evaluate the efficacy of the therapy parameter sets. As an example chronic pain may cause a patient to avoid particular activities, high levels of activity, or activity in general. Systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to associate activity levels and metrics with therapy parameter sets for delivery of such therapies, and thereby evaluate the extent to which a therapy parameter set is alleviating chronic pain by evaluating the extent to which the therapy parameter set improves the overall activity level of the patient.

As another example, mood disorders, and particularly depression, may cause a patient to be inactive, despite a physical ability to be active. Often, a patient with depression will spend the significant majority of his or her day in bed. Systems according to the invention may include any of a variety of medical devices that deliver any of a variety of therapies to treat a mood disorder, such as DBS, cranial nerve stimulation, peripheral nerve stimulation, vagal nerve stimulation, or one or more drugs. Systems may use the techniques of the invention described above to associate activity levels and metrics with therapy parameter sets for delivery of such therapies, and thereby evaluate the extent to which a therapy parameter set is alleviating the mood disorder by evaluating the extent to which the therapy parameter set improves the overall activity level of the patient.

Movement disorders, such as tremor and Parkinson's disease may also affect the overall activity level of a patient. Further, movement disorders are also characterized by irregular, uncontrolled and generally inappropriate movements, e.g., tremor or shaking, particularly of the limbs. In addition to using the sensors described above to sense the overall activity level of a movement disorder patient, some embodiments of the invention may use such sensors to detect the types of inappropriate movements associated with the movement disorder. For example, accelerometers, piezoelectric crystals, or EMG electrodes located in the trunk or limbs of a patient may be able to detect inappropriate movements such as tremor. Such detection may also be used to detect epileptic seizures or symptoms of neurological disorders.

Systems according to the invention may periodically determine the level or severity of such movements based on the signals output by such sensors, associate the inappropriate movement levels with current therapy parameter sets, and determine activity metric values for therapy parameter sets based on the associated levels. For example, a processor of such a system may determine a frequency or amount of time that such movements exceeded a threshold during delivery of a therapy parameter set as an inappropriate movement based activity metric value for the therapy parameter set. Another type of inappropriate movement associated particularly with Parkinson's disease is "gait freeze," which will be discussed in greater detail below.

Systems according to the invention may include any of a variety of medical devices that deliver any of a variety of therapies to treat a movement disorders (or other neurological disorders), such as DBS, cortical stimulation, or one or more drugs. Systems may use the techniques of the invention described above to associate overall activity levels and metrics, as well as inappropriate movement levels and inappropriate movement activity metrics, with therapy parameter sets for delivery of such therapies. In this manner, such system may allow a user to evaluate the extent to which a therapy parameter set is alleviating the movement disorder by evaluating the extent to which the therapy parameter set improves the overall activity level of the patient and/or decreases the extent of inappropriate movements by the patient.

Further, some ailments and symptoms, such as movement disorders and chronic pain, may affect the gait of a patient. More particularly, such symptoms and ailments may result in, as examples, an arrhythmic, asymmetric (left leg versus right leg), or unusually variable gait, or a gait with relatively short stride lengths. Systems according to the invention may use sensors discussed above that output signals as a function of activity, and particularly as a function of footfalls or impacts, to monitor gait. For example, systems according to the invention may use one or more accelerometers or piezoelectric crystals located on or within the trunk or legs of the patient to monitor gait.

A processor of such a system may periodically determine a value for asymmetry, variability, or stride length of gait, and associate such values with a current therapy parameter set used to deliver any of the therapies discussed herein with reference to chronic pain or movement disorders. The processor may determine an activity metric value based on gait by, for example, averaging the gait values associated with a therapy parameter set over a period of time, such as a day, week or month. The processor of the system that performs the techniques of the invention, such as gait monitoring and activity metric determination, may include one or more of a processor of an IMD or a processor of a programming or computing device, as discussed above.

As discussed above, the techniques of the invention may be used to evaluate therapy parameter sets used by a medical device to deliver therapy to treat movement disorders, such a Parkinson's disease. One symptom that most commonly associated with Parkinson's disease is "gait freeze." Gait freeze may occur when a Parkinson's patient is walking. Gait freeze refers to a relatively sudden inability of a Parkinson's patient to take further steps. Gait freeze is believed to result from a neurological failure and, more specifically, a failure in the neurological signaling from the brain to the legs. A device according to embodiments of the invention may determine when gait freeze has occurred and store information regarding the occurrence of the gait freeze.

FIG. 10 is a block diagram illustrating an example system 10C including an IMD 14C that collects activity information, including gait regularity information, and further identifies and responds to gait freeze events. System 10C and IMD 14C may be substantially similar to systems 10A and 10B, and IMDs 14A and 14B, described above. IMD 14C is coupled to leads 16F and 16G, which include electrodes 42Q-X. The electrodes may be implanted, for example, proximate to the spinal cord, or on or within the brain of a patient 12, as described above. Although not illustrated in FIG. 10, IMD 14C may include a multiplexer 52 and EEG signal module 54.

System 10C, e.g., processor 46 of IMD 14C, may use sensors 40 to determine activity levels and activity metric values for various therapy parameter sets in the manner discussed above. Additionally, system 130 monitors gait regularity, and detects gait freeze events based on the signals output by sensors 40.

For example, processor 46, or another processor of the system, may detect a relatively sudden cessation of activity associated with a gait event based on the output of accelerometers, piezoelectric crystals, EMG electrodes, or other sensors that output signals based on footfalls or impacts associated with, for example, walking. When experiencing a gait freeze event, a patient may "rock" or "wobble" while standing in place, as if attempting unsuccessfully to move. In some embodiments, processor 46 may monitor any of sensors 40 that output signals as a function of posture discussed above, such as a 3-axis accelerometer, to detect the minor, rhythmic changes in posture associated with rocking or wobbling. Processor 46 may detect a gait freeze event when it occurs based on one or more of the posture or activity sensors. For example, processor 46 may confirm that a relatively sudden cessation of activity is in fact a gait freeze event based on rocking or wobbling indicated by posture sensors.

Further, in some embodiments, the processor may detect a gait freeze prior to onset. For example, sensors 40 may include EMG or EEG electrodes, and processor 46 may detect a gait freeze prior to onset based on irregular EMG or EEG activity. EMG signals, as an example, demonstrate irregularity just prior to a freezing episode, and a processor may detect this irregularity as being different from the EMG signals typically associated with walking. In other words, a walking patient may exhibit normal EMG pattern in the legs, which may be contrasted with EMG activity and timing changes that precede freezing.

In general, EMG signals from right and left leg muscles include a regularly alternating rhythm pattern that characterizes normal gait. When the "timing" of the pattern fails, there is no longer a regular rhythm, and a gait freeze may result. Accordingly, a processor may detect irregularity, variability, or asymmetry, e.g., within and between right and left leg muscles, in one or more EMG signals, and may detect an oncoming gait freeze prior to occurrence based on the detection. In some embodiments, the processor may compare the EMG signals to one or more thresholds to detect gait freeze. Comparison to a threshold may, for example, indicate an absolute value or increase in irregularity, variability, or asymmetry that exceeds a threshold, indicating an oncoming gait freeze. In some embodiments, thresholds may be determined based on EMG signal measurements made when the patient is walking normally.

Whether gait freeze is detected prior to or during occurrence, the processor may associate the occurrence of the gait freeze event and/or its length with a current therapy parameter set used to control delivery of a therapy for Parkinson's disease, such as DBS or a drug. Additionally, the processor may determine or update an activity metric value for the therapy parameter set based on the gait freeze event, such as a total number of gait freeze events for the therapy parameter set, an average number of gait freeze events over a period of time, or an average length of a gait freeze event.

In some embodiments, in addition to recording gait freeze events and determining activity metric values based on such events, the processor may control delivery of a stimulus to terminate the gait freeze event. For example, in embodiments in which leads 16 are implanted on or within the brain of the patient, processor 46 may control delivery of a therapeutic stimulation to terminate the gait freeze. Further, in embodiments in which leads 16 are implanted proximate to the spinal cord or peripheral nerves, or within muscle, processor 46 may control delivery of stimulation perceivable by the patient to "prompt" the patient to walk, thereby terminating the gait freeze. The stimulation may be rhythmic, e.g., may approximate the rhythm of walking, which may prompt the patient to walk and thereby terminate the gait freeze.

In some embodiments, such as embodiments in which leads are not located in the above-identified positions, IMD 10C may include a gait cue module 130, which processor 46 may control to deliver such stimulation. Gait cue module 134 may provide stimuli as gait clues, such as audible or otherwise perceivable vibration or electrical stimulus, which may be rhythmic. In embodiments in which processor 46 detects a gait freeze prior to onset, the processor may control delivery of such stimuli prior to onset to avoid the occurrence of the gait freeze event.

Further, in some embodiments, a processor of a different device within system 130, such as a processor of a patient programmer 26 (FIG. 1), detects the gait freeze based on signals generated by sensors 40, or an indication received from processor 46 via telemetry circuitry 50. In such embodiments, the other device may include a gait cue module 130 that provides any of the stimuli or gait cues described above, such as rhythmic audible prompts. Further, a gait cue module 130 in an external programmer or other device may provide other gate cues, such as visual prompts via a display or a projected image of footprints via a projector. The processor may direct the gait cue module 130 to provide such gate cues in response to an anticipated or detected gate freeze event.

Figure 11:
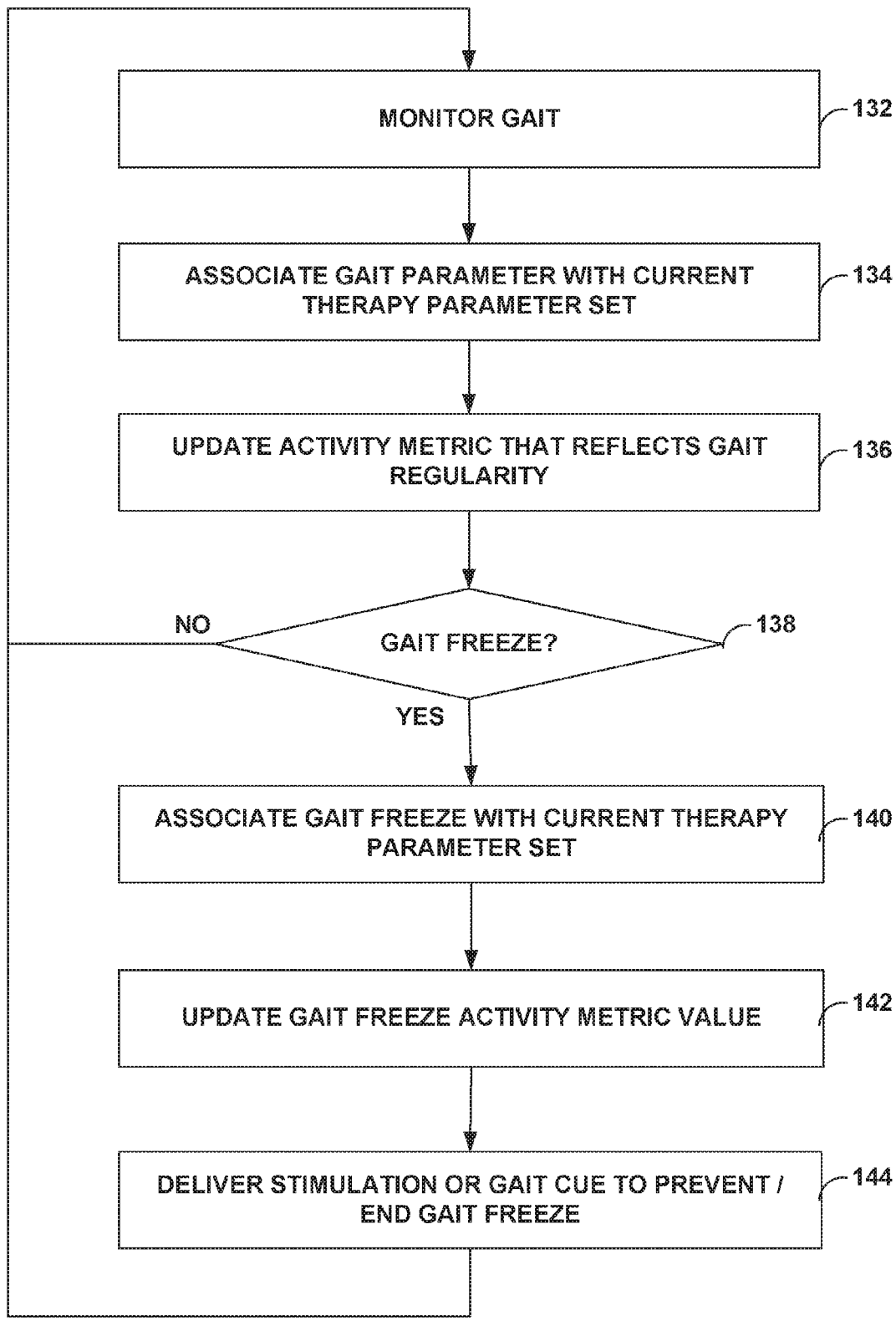
FIG. 11 is a flow diagram illustrating an example method for monitoring gait regularity, and identifying and responding to gait freeze events.

FIG. 11 is a flow diagram illustrating an example method for monitoring gait regularity, and identifying and responding to gait freeze events. According to the example method, a processor monitors the gait of a patient based on signals from one or more sensors, such as one or more three-axis accelerometers or piezoelectric crystals (132). The processor may periodically determine a gait regularity parameter value (134). The gait regularity parameter value may be a gait asymmetry value, a gait arrhythmicity value, a gait variability value, or a stride length. The parameter value may be a numerical value indicative of the extent of gait regularity, e.g., symmetry, rhythmicity or variability, such as a number between zero and one, where one indicates normal gait regularity, symmetry, rhythmicity, or variability. The processor may identify a therapy parameter set currently used to deliver therapy to the patient when the gait regularity parameter value was determined, such as a therapy for treatment of Parkinson's disease, and may update an activity metric for the therapy parameter set that reflects gait regularity based on the determined gait regularity parameter value (136). The gait regularity activity metric may, for example, by an average of determined gait parameter values for the therapy parameter set. As other examples, the gait regularity activity metric may reflect comparison of the gait regularity number, e.g., a symmetry, rhythmicity, or variability number, or a stride length, to a threshold, such as an amount or percentage of time that the value was above or below a threshold.

If the processor detects a gait freeze event based on signals from the one or more sensors (138), the processor associates the gate freeze event with a therapy parameter set currently used to control delivery of a therapy (140). The processor determines or updates a gait freeze activity metric value for the therapy parameter set based on the detection (142). The gait freeze activity metric may be, for example, a number of gait freeze events per unit time that the therapy parameter set was active, such as the number of gait freezes per day.

The processor also controls or requests delivery of stimulation or a gait cue to prevent or terminate or overcome the gait freeze event (144). In alternative embodiments, the processor may only identify and log gait freeze events for review at a later time by a clinician. In addition, the gait freeze metric may be reviewed at a later time and used to adjust current therapy programs or create new therapy programs.

FIG. 12 illustrates an example list 145 of therapy parameter sets and associated activity metric values relating to patient gait which may be presented by a clinician programmer. Similar to list 90 of FIG. 7, each row of example list 145 includes an identification of one of therapy parameter sets 60, the parameters of the therapy parameter set, and activity metric values 66 associated with the therapy parameter set for each of two illustrated activity metrics. Programmer 20 may order list 145 according to a user-selected one of the activity metrics.

The activity metrics illustrated in FIG. 12 are an average gait regularity value, expressed as a numerical value between zero and one, and an average number of gait freeze events per day. An IMD 14 or programmer 20 may determine the average number of gait freeze events per day for one of the illustrated therapy parameter sets by identifying the total number of gait freeze events associated with the parameter set and the total amount of time that the IMD 14 was using the parameter set.

Figure 13:
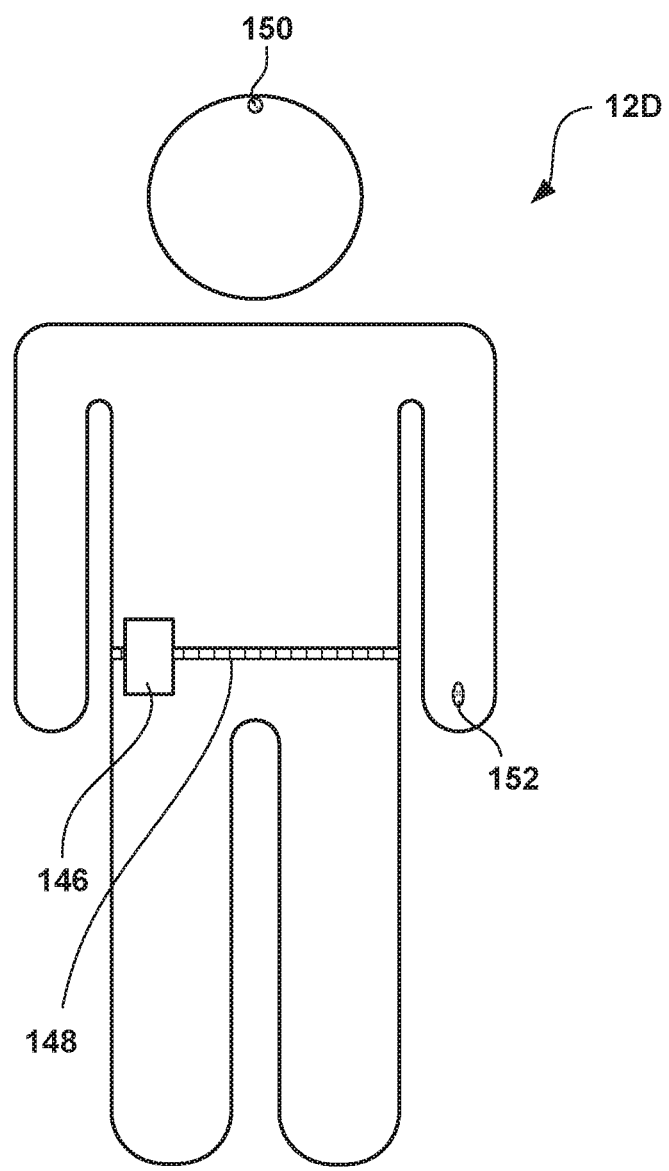
FIG. 13 is a conceptual diagram illustrating a monitor that monitors values of one or more accelerometers.

FIG. 13 is a conceptual diagram illustrating a monitor that monitors values of one or more accelerometers of the patient instead of, or in addition to, a therapy delivering medical device. As shown in FIG. 13, patient 12D is wearing monitor 146 attached to belt 148. Monitor 146 is capable of receiving measurements from one or more sensors located on or within patient 12D. In the example of FIG. 13, accelerometers 150 and 152 are attached to the head and hand of patient 12D, respectively. Accelerometers 150 and 152 may measure movement of the extremities, gait, or general activity level, of patient 12D. Alternatively, more or less accelerometers or other sensors may be used with monitor 146. Accelerometers 150 and 152 may be used to detect gait regularity, gait freeze or other movement abnormalities associated with neurological disorders, using the techniques described above. Monitor 146 or some other device may determine any of the variety of activity metrics described above based on the signals generated by accelerometers 150 and 152. In some embodiments, accelerometers positioned similarly to the manner illustrated with respect to accelerometers 150 and 152 in FIG. 13 may be included in system 10C from FIG. 10.

Accelerometers 150 and 152 may be preferably multi-axis accelerometers, but single-axis accelerometers may be used. As patient 12D moves, accelerometers 150 and 152 detect this movement and send the signals to monitor 146. High frequency movements of patient 12D may be indicative of tremor, Parkinson's disease, or an epileptic seizure, and monitor 146 may be capable of indicating to an IMD 14, for example, that stimulation therapy must be changed to effectively treat the patient. Conversely, the sudden stop of movement may indicate gait freeze in patient 12D. In addition, accelerometers 150 and 152 may detect the activity of patient 12D in addition to or instead of other sensors. Accelerometers 150 and 152 may be worn externally, i.e., on a piece of clothing or a watch, or implanted at specific locations within patient 12D. In addition, accelerometers 150 and 152 may transmit signals to monitor 146 via wireless telemetry or a wired connection.

Monitor 146 may store the measurements from accelerometers 150 and 152 in a memory. Monitor 146 may analyze the measurements using any of the techniques described herein. In some examples, monitor 146 may transmit the measurements from accelerometers 150 and 152 directly to another device, such as an IMD 14, programming device 20,26, or other computing device. In this case, the other device may analyze the measurements from accelerometers 150 and 152 to detect efficacy of therapy or control the delivery of therapy.

In some examples, a rolling window of time may be used when analyzing measurements from accelerometers 150 and 152. Absolute values determined by accelerometers 150 and 152 may drift with time or the magnitude and frequency of patient 12D movement may not be determined by a preset threshold. For this reason, it may be advantageous to normalize and analyze measurements from accelerometers 150 and 152 over a discrete window of time. For example, the rolling window may be useful in analyzing the gait of patient 12D. Movements that stop or are erratic for a predetermined period of time may be detected in a rolling window. Monitor 146 may even be able to predict gait freeze if a certain pattern of movement is detected over a certain time frame defined by the rolling window. In this manner, a few quick movements or lack of movement from patient 12D not associated with gait freeze may not trigger a response and change in therapy. The rolling window may also be used in detecting changes in activity with accelerometers 150 and 152 or other sensors as described herein.

Figure 14:
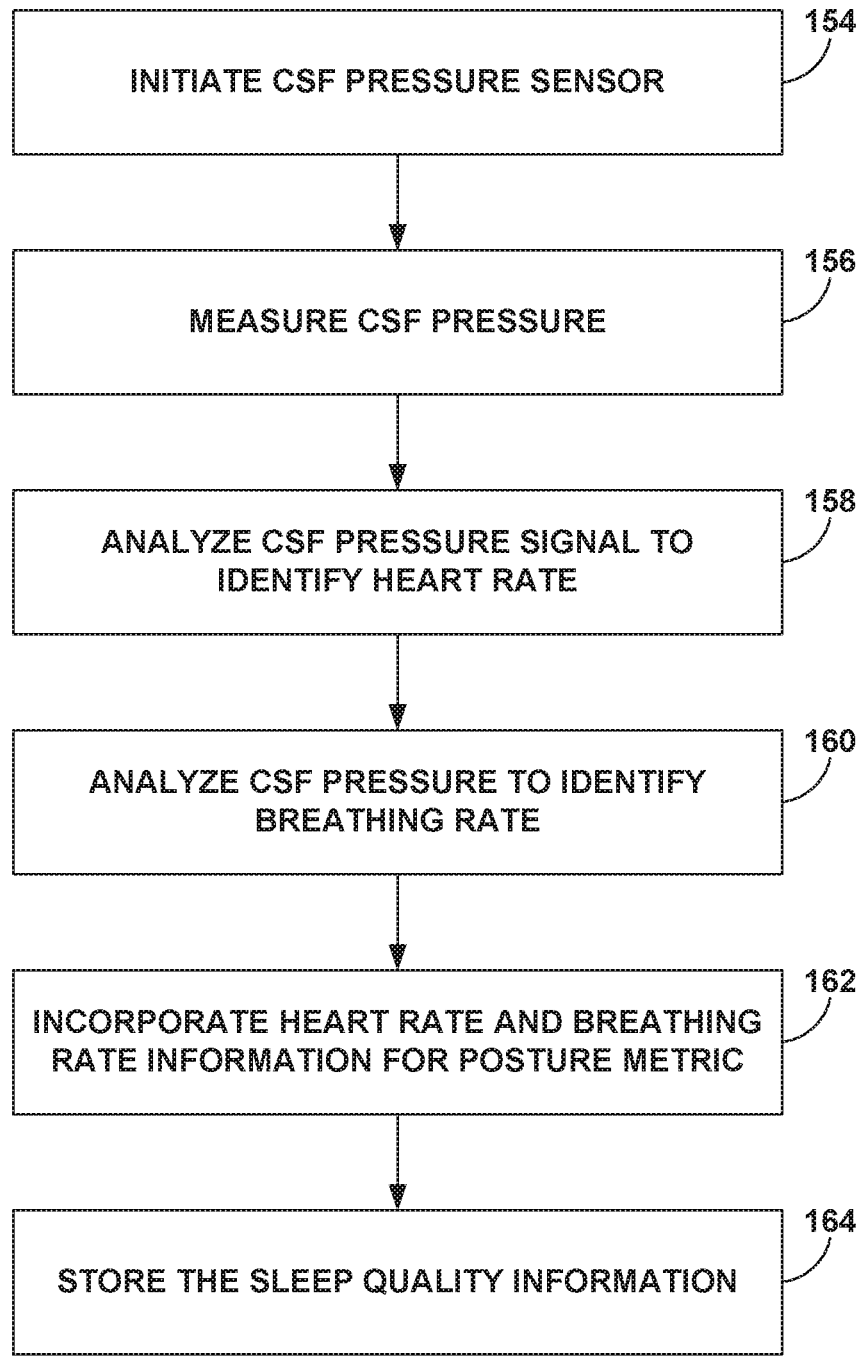
FIG. 14 is a flow diagram illustrating monitoring the heart rate and breathing rate of a patient by measuring cerebral spinal fluid pressure.

FIG. 14 is a flow diagram illustrating monitoring the heart rate and breathing rate of a patient by measuring cerebral spinal fluid pressure. As shown in FIG. 14, a physiological parameter that may be measured in patient 12D is heart rate and respiration, or breathing, rate. Specifically, cerebral spinal fluid (CSF) pressure may be analyzed to monitor the heart rate and breathing rate of patient 12D. A clinician initiates a CSF pressure sensor to being monitoring heart rate and/or breathing rate (154). Alternatively, the CSF pressure sensor may be implanted within the brain or spinal cord of patient 12D to acquire accurate pressure signals. The CSF pressure sensor must also store the pressure data or begin to transfer pressure data to an implanted or external device. As an example used herein, the CSF pressure sensor transmits signal data to an IMD 14.

Once the CSF pressure sensor is initiated, the CSF pressure sensor measures CSF pressure and transmits the data to an IMD 14 (156). An IMD 14 analyzes the CSF pressure signal to identify the heart rate (158) and breathing rate (160) of patient 12D. The heart rate and breathing rate can be identified within the overall CSF pressure signal. Higher frequency fluctuations (e.g. 40 to 150 beats per minute) can be identified as the heart rate while lower frequency fluctuations (e.g. 3 to 20 breaths per minute) in CSF pressure are the breathing rate. An IMD 14 may employ filters, transformations, or other signal processing techniques to identify the heart rate and breathing rate from the CSF pressure signal.

An IMD 14 may utilize the heart rate and breathing rate information as additional information when determining the activity metric of patient 12D (162). For example, faster heart rates and faster breathing rates may indicate that patient 12D is standing or active. IMD 14 may then store the activity metric or use it to adjust stimulation therapy (164).

Various embodiments of the invention have been described. However, one skilled in the art will recognize that various modifications may be made to the described embodiments without departing from the scope of the invention. For example, the invention may be embodied as a computer-readable medium that includes instructions to cause a processor to perform any of the methods described herein. These and other embodiments are within the scope of the following claims.

What is claimed is:

1. A method comprising:
   monitoring, with an implantable medical device, a physiological signal of a patient based on a signal generated by an implantable sensor within the patient;
   predicting, with the implantable medical device, a gait freeze event based on the signal prior to onset of the gait freeze event; and
   providing a gait cue indicative of the predicted gait freeze event to the patient.

2. The method of claim 1, wherein providing a gait cue indicative of the predicted gait freeze event to the patient comprises providing, by the implantable medical device, a gait cue indicative of the predicted gait freeze event to the patient.

3. The method of claim 1, wherein the gait cue is a perceivable vibration.

4. The method of claim 1, wherein the gait cue is an electrical stimulus.

5. The method of claim 1, wherein the gait cue is a visual prompt.

6. The method of claim 1, wherein the gait cue is an audible stimulus.

7. The method of claim 1,
   wherein the signal generated by the implantable sensor includes an electromyogram (EMG) signal, and
   wherein predicting, with the implantable medical device, the gait freeze event based on the signal includes predicting the gait freeze event based on irregular EMG activity in the EMG signal.

8. The method of claim 1,
   wherein the signal generated by the implantable sensor includes an electroencephalogram (EEG) signal, and
   wherein predicting, with the implantable medical device, the gait freeze event based on the signal includes predicting the gait freeze event based on irregular EEG activity in the EEG signal.

9. The method of claim 1, wherein predicting, with the implantable medical device, the gait freeze event based on the signal includes:
   monitoring a gait of the patient based on the signal generated by the implantable sensor; and
   anticipating, with the implantable medical device, the gait freeze event based on the signal.

10. The method of claim 1, wherein predicting, with the implantable medical device, the gait freeze event based on the signal includes:
    monitoring a gait of the patient based on the signal generated by the implantable sensor; and
    detecting, with the implantable medical device, the gait freeze event based on the signal.

11. The method of claim 1, wherein monitoring the physiological signal of the patient includes monitoring the physiological signal of the patient with one or more electrodes of the implantable sensor.

12. The method of claim 1, wherein monitoring the physiological signal of the patient includes sensing activity via an activity sensor.

13. A system comprising:
    an implantable sensor configured to generate a signal that varies as a function of activity of a patient;
    a processor configured to monitor a physiological signal of a patient based on the signal generated by the implantable sensor and predicts a gait freeze event based on the signal prior to onset of the gait freeze event; and
    a gait cue module configured to provide a gait cue indicative of the predicted gait freeze event to the patient.

14. The system of claim 13, wherein the gait cue is a perceivable vibration.

15. The system of claim 13, wherein the gait cue is an electrical stimulus.

16. The system of claim 13, wherein the gait cue is a visual prompt.

17. The system of claim 13, wherein the gait cue is an audible stimulus.

18. The system of claim 13,
wherein the signal generated by the implantable sensor includes an electromyogram (EMG) signal, and
wherein the processor is configured to predict the gait freeze event based on irregular EMG activity in the EMG signal.

19. The system of claim 13,
wherein the signal generated by the implantable sensor includes an electroencephalogram (EEG) signal, and
wherein the processor is configured to predict the gait freeze event based on irregular EEG activity in the EEG signal.

20. A non-transitory computer-readable storage medium comprising instructions that cause a processor to:
monitor a physiological signal of a patient based on a signal generated by an implantable sensor within the patient;
predict a gait freeze event based on the signal prior to onset of the gait freeze event; and
issue instructions to a gait cue module to provide a gait cue indicative of the predicted gait freeze event to the patient.

\* \* \* \* \*